US006864396B2

(12) United States Patent
Smith et al.

(10) Patent No.: US 6,864,396 B2
(45) Date of Patent: Mar. 8, 2005

(54) SUBSTITUTED PENTACENE SEMICONDUCTORS

(75) Inventors: Terrance P. Smith, Woodbury, MN (US); Dennis E. Vogel, Lake Elmo, MN (US); Kim M. Vogel, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/256,616

(22) Filed: Sep. 27, 2002

(65) Prior Publication Data

US 2003/0105365 A1 Jun. 5, 2003

Related U.S. Application Data

(63) Continuation-in-part of application No. 09/966,961, filed on Sep. 27, 2001, now abandoned.
(51) Int. Cl.$^7$ .............................................. C07C 43/20
(52) U.S. Cl. ......................... 568/633; 568/58; 568/632; 568/634; 570/183; 585/26; 257/40
(58) Field of Search ........................... 257/40; 568/632, 568/633, 634, 58; 570/183; 585/26

(56) References Cited

U.S. PATENT DOCUMENTS

| | | | |
|---|---|---|---|
| 3,627,655 A | 12/1971 | Perez-Albuerne | |
| 5,707,779 A | 1/1998 | Naito | 430/270.1 |
| 6,165,383 A | 12/2000 | Chou | 252/301.16 |
| 6,465,116 B1 | 10/2002 | Ishikawa et al. | 428/690 |
| 6,489,046 B1 * | 12/2002 | Ikeda et al. | 428/690 |

FOREIGN PATENT DOCUMENTS

| | | | |
|---|---|---|---|
| EP | 0 726 304 A2 | 8/1996 | C09K/11/16 |
| EP | 0 786 820 A2 | 7/1997 | H01L/51/20 |
| JP | 63-199759 | 8/1988 | C09B/5/02 |
| JP | 11-354277 | 12/1999 | H05B/33/14 |
| WO | WO 00/03565 | 1/2000 | H05B/33/00 |
| WO | WO 00/56933 | 9/2000 | C12Q/1/68 |
| WO | WO 01/45469 A1 | 6/2001 | H05B/33/14 |
| WO | WO 03/016599 A1 | 2/2003 | C30B/29/54 |

OTHER PUBLICATIONS

B. Hulin et al., "A Convenient, Mild Method for the Cyclization of 3– and 4–Arylalkanoic Acids via Their Trifluoromethanesulfonic Anhydride Derivatives", J. Org. Chem., vol. 49, (1984), pp. 207–209.

T. Yamato et al., "Organic Reactions Catalyzed by Solid Superacids. 5.$^1$Perfluorinated Sulfonic Acid Resin (Nafion–H) Catalyzed Intramolecular Friedel–Crafts Acylation", J. Org. Chem., vol. 56, No. 12, (1991), pp. 3955–3957.

V. Premasagar et al., "Methanesulfonic Acid Catalyzed Cyclization of 3–Arylpropanoic and 4– Arylbutanoic Acids to 1–Indanones and 1–Tetralones", J. Org. Chem., vol. 46, No. 14, (1981), pp. 2974–2976.

Mills and Mills: The Synthetical Production of Derivatives of Dinaphthanthracene "CCXXX.—*The Synthetical Production of Derivatives of Dinaphthanthracene*", J. Chem. Soc., vol. 101, (1912), pp. 2194–2208.

J. M. Shaw et al., "*Organic Electronics: Introduction*", IBM J. Res. & Dev., vol. 45, No. 1, (Jan. 2001), pp. 3–9.

C. D. Dimitrakopoulos et al., "*Organic Thin–Film Transistors: A Review of Recent Advances*", IBM J. Res. & Dev., vol. 45, No. 1, (Jan. 2001), pp. 11–27.

C. D. Dimitrakopoulos et al., "*Molecular Beam Deposited Thin Films of Pentacene for Organic Field Effect Transistor Applications*", J. Appl. Phys., vol. 80, No. 4, (Aug. 15, 1996), pp. 2501–2508.

D. J. Gundlach et al., "*Solvent–Induced Phase Transition in Thermally Evaporated Pentacene Films*", Appl. Phys. Lett., vol. 74, No. 22, (May 31, 1999), pp. 3302–3304.

Y.–Y. Lin et al., "*Stacked Pentacene Layer Organic Thin–Film Transistors with Improved Characteristics*" IEEE Electron Device Letters, vol. 18, No. 12, (Dec. 1997), pp. 606–608.

A. Orita et al., "*Integrated Chemical Process: One–Pot Aromatization of Cyclic Enones by the Double Elimination Methodology*" Angew. Chem. Int. Ed., vol. 38, No. 15, (1999) pp. 2267–2270.

A. R. Wartini et al., "*Intramolecular Electron Transfer Between Terminal 1,4–Dimethoxybenzene Units in Radical Cations with a [2.2](1,4)Naphthalenophane, [2.2](1,4)Anthracenophane, and Pentacene Skeleton*", Eur. J. Org. Chem., (1998), pp. 1161–1170.

Kirk–Othmer Enc. Of Chemical Technology, "*Friedel–Crafts Reactions*", vol. 11, 4$^{th}$ ed., John Wiley & Sons, Inc., NY, (1994), pp. 1043–1075.

* E. Philippi et al., "*Dinaphthanthracene Series V, VI*", Monatshefte Fur Chemie, vol. 43, (1923), pp. 615–619.

* E. Philippi, "*Synthesis of Linear Diphthaloyl Benzene*", Monatshefte Fur Chemie, vol. 32, (1911), pp. 631–635.

(List continued on next page.)

Primary Examiner—Rosalynd Keys
(74) Attorney, Agent, or Firm—Lisa P. Fulton

(57) ABSTRACT

Substituted pentacene compounds comprise at least one substituent selected from the group consisting of electron-donating substituents, halogen substituents, and combinations thereof; the substituent(s) each being bonded to a carbon atom of a terminal ring of pentacene, and being the only substituent(s); with the proviso that when the compound has only two substituents, both of which are methyl or alkoxy, and one substituent is bonded to the number 2 carbon atom, the other substituent, if methyl, is bonded to the number 1, 3, 4, 8, or 11 carbon atom and, if alkoxy, is bonded to the number 1, 3, 4, 8, 9, or 11 carbon atom; and with the further proviso that when the compound has only four substituents, all of which are alkoxy, the substituents are bonded to the numbers 2, 3, 9, and 10 carbon atoms.

24 Claims, No Drawings

OTHER PUBLICATIONS

E. Philippi, "*Condensation of Pyromellitic Anhydride with Benzene and Toluene*", Monatshefte Fur Chemie, vol. 34, (1913), pp. 705–715.

\* E. Philippi et al., "*Dinaphthanthracene Series IV Bromo Derivatives*", Monatshefte Fur Chemie, vol. 42, (1921), pp. 1–4.

\* G. Machek, "*Linear Pentacene Series XIX Constitution of the Bi–derivatives of 5,7,12,14–Pentacenediquinone*", Monatshefte Fur Chemie, vol. 56, (1930), pp. 116–134.

H. E. Katz et al., "*Synthetic Chemistry for Ultrapure, Processable, and High–Mobility Organic Transistor Semiconductors*", American Chemical Society, Accounts of Chemical Research, vol. 34, No. 5, (2001), pp. 359–369.

S. M. Sze, *Physics of Semiconductor Devices*, MOSFET Structures, 8.5.6 Thin–Film Transistor, $2^{nd}$ ed., John Wiley & Sons, (1981), pp. 492–493.

S. M. Sze, *Physics of Semiconductor Devices*, MOSFET Basic Device Characteristics, 8.2.2 Linear and Saturation Regions, $2^{nd}$ ed., John Wiley & Sons, (1981), pp. 438–442.

J.M. Allen et al., "*Friedel–Crafts Cyclisation–VI[1] Polyphosphoric Acid Catalysed Reactions of Crotonophenones and Chalcones*", Tetrahedon, vol. 33, (1977), pp. 2083–2087.

\*H. de Diesbach et al. "*Derivatives of Dinaphthanthracene Diquinone and the Synthesis of Dinaphthaleneanthracene Diquinone*", Helvetica Chim. Acta, vol. 7, (1924), pp. 644–653.

E. Clar et al., "*Information on Polycyclic Aromatic Hydrocarbons and Their Derivatives, V. Naphthoanthracene, Their Oxidation Products and a New Class of Deep–Colored Hydrocarbons*", Chem Berichte, (1929), 3027–3032.

E. Clar et al., "*Information on Polycyclic Aromatic Hydrocarbons and Their Derivatives, II. [Naphtho–2', 3': 1,2–anthracene][1]), its Homologues and its Oxidation Products*", Chem Berichte, (1929), p. 940–947.

E. Clar et al., "*Information on Polycyclic Aromatic Hydrocarbons and Their Derivatives, VIII. [Naphtho–2',3':1,2–anthracene], [2,3:6,7–dibenzoanthracenes–9,10–diyls]and Their Oxidation Products*", Chem. Berichte, (1929), p. 981–986.

F. Effenberger et al., "*Catalytic Friedel–Crafts Acylation of Aromatic Compounds*", Angew. Chem. Internat, Edit., vol. 11, No. 4 (1972), pp. 300–301.

G. A. Olah et al., "*Nafion–H Catalysed Intramolecular Friedel–Crafts Acylation: Formation of Cyclic Ketones and Related Heterocycles*", Synlett, No. 7, (1999), pp. 1067–1068.

S. Miki et al., "*Synthesis of 1,2,3–Tri–t–butyl–6,13– and 8,9,10–Tri–t–butyl–5,14–pentacenequinones and Their Photochromic Behaviors: New Photochromic Molecules*", Tetrahedron, vol. 52, No. 12, (1996), pp. 4269–4276.

T. Takahashi, et al., "*Straightforward Method for Synthesis of Highly Alkyl–Substituted Naphthacene and Pentacene Derivatives by Homologation*", J. Am. Chem. Soc., (2000), pp. 12876–12877, vol. 22.

\* cited by examiner

SUBSTITUTED PENTACENE SEMICONDUCTORS

STATEMENT OF PRIORITY

This application is a continuation-in-part of application Ser. No. 09/966,961 filed Sep. 27, 2001, now abandoned, and claims the priority thereof.

FIELD

This invention relates to organic compounds that are useful as semiconductors and, in another aspect, to devices comprising the compounds.

BACKGROUND

Traditionally, inorganic silicon and gallium arsenide semiconductors, silicon dioxide insulators, and metals such as aluminum and copper have dominated the semiconductor industry. In recent years, however, there has been an increasing research effort in using organic thin-film transistors (OTFTs) as an alternative to the traditional thin-film transistors based on inorganic materials.

Pentacene, thiophene oligomers, and regioregular polythiophenes have been the most widely researched organic semiconductors. Of these classes of semiconducting organic materials, the highest charge-carrier mobility values have been observed for pentacene. Charge-carrier mobility values greater than 1.5 cm$^2$ V$^{-1}$ s$^{-1}$, on/off current ratios greater than 10$^8$, and sub-threshold voltages of less than 1.6 V have been reported for pentacene-based transistors. These values are comparable or superior to those of amorphous silicon-based devices.

However, the performance of pentacene-based devices can be difficult to reproduce. This lack of reproducibility is due to the polymorphic nature of pentacene. The alignment or structural order of the pentacene molecules differs for each polymorph or crystallographic phase, and this structural order determines the electronic properties of the device. The crystallographic phase adopted by pentacene depends on the process and conditions under which the crystals are formed. For example, when pentacene is vapor-deposited onto a substrate, a thin film phase is formed. This thin film phase is more effective at transporting charge than pentacene's bulk or single crystal phase, but it is meta-stable. For example, the thin film form of pentacene can be converted to the bulk phase by exposure to solvents such as isopropanol, acetone or ethanol. (See, for example, Gundlach et al., Applied Physics Letters, 74(22) 3302 (2000).)

In order to achieve maximum performance, pentacene must generally be deposited from the vapor phase by vacuum sublimation. The vacuum sublimation process, however, requires expensive equipment and lengthy pump-down cycles. Solution processing has the potential to greatly reduce the manufacturing costs associated with the use of organic semiconductors. Pentacene, however, is insoluble in common solvents and is therefore not a good candidate for solution processing.

SUMMARY

In view of the foregoing, we recognize that there is a need for organic semiconductors that can provide stable, reproducible electronic performance characteristics and that exhibit charge-carrier mobilities comparable to or better than those of pentacene. Furthermore, we recognize that it would be advantageous to have an organic semiconductor with increased solubility in common organic solvents and therefore increased suitability for solvent processing.

Briefly, in one aspect, the present invention provides substituted pentacene compounds that are useful as organic semiconductors. The compounds comprise at least one substituent selected from the group consisting of electron-donating substituents (for example, alkyl, alkoxy, or thioalkoxy), halogen substituents, and combinations thereof; the substituent(s) each being bonded to at least one carbon atom of a terminal ring of pentacene (that is, a carbon atom selected from the number 1, 2, 3, 4, 8, 9, 10, and 11 carbon atoms of pentacene) and being the only substituent(s) (that is, hydrogen is bonded to the carbon atoms of the non-terminal rings, as well as to any carbon atom of a terminal ring that does not bear a substituent); with the proviso that when the compound has only two substituents, both of which are methyl or alkoxy, and one substituent is bonded to the number 2 carbon atom of pentacene, the other substituent, if methyl, is bonded to the number 1, 3, 4, 8, or 11 carbon atom and, if alkoxy, is bonded to the number 1, 3, 4, 8, 9, or 11 carbon atom; and with the further proviso that when the compound has only four substituents, all of which are alkoxy, the substituents are bonded to the numbers 2, 3, 9, and 10 carbon atoms.

Preferably, the compounds are disubstituted (more preferably, 2,9- or 2,10-disubstituted; most preferably, 2,9-disubstituted).

It has been discovered that the above-described compounds surprisingly exhibit charge-carrier mobilities comparable to those of pentacene, in spite of the addition of insulating substituents. These mobilities (measured for OTFTs comprising the compounds of the invention) of approximately 0.2 to 0.7 cm$^2$ V$^{-1}$ s$^{-1}$ are comparable to those of highly crystalline pentacene. Devices comprising the compounds also appear to exhibit more reproducible performance characteristics than those of pentacene-based devices. Exposure to common organic solvents, such as isopropanol, for example, does not appear to significantly alter the electronic properties of the devices. In addition, at least some of the compounds of the invention are more soluble than pentacene in organic solvents and are therefore better candidates for economical solution processing methods of deposition.

Thus, the compounds of the invention meet the need in the art for organic semiconductors that can provide charge-carrier mobilities comparable to those of pentacene, while also exhibiting improved electronic stability and reproducibility of performance characteristics in a semiconductor device.

In other aspects, this invention also provides semiconductor devices comprising at least one compound of the invention; semiconductor devices comprising at least one of 2,9-dimethylpentacene, 2,10-dimethylpentacene, 2,10-dialkoxypentacenes, and 1,4,8,11-tetraalkoxypentacenes; and articles comprising the semiconductor devices.

DETAILED DESCRIPTION

Compounds

Compounds with fused aromatic ring systems are commonly given a numbering sequence in which each carbon atom that is a member of only one ring is numbered. (See, for example, James E. Banks, NAMING ORGANIC COMPOUNDS: A PROGRAMMED INTRODUCTION TO ORGANIC CHEMISTRY, Saunders College Publishing, p. 124, PA (1976).) The numbering sequence that is generally used for pentacene, for example, is shown below.

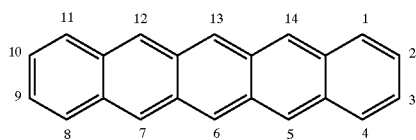

Formula I

The location of a substituent on such a compound is commonly specified by reference to the number of the carbon atom to which the substituent is bonded. There is one hydrogen atom bonded to each numbered carbon atom if no substituent is indicated.

The substituted pentacene compounds of the invention comprise at least one substituent selected from the group consisting of electron-donating substituents, halogen substituents, and combinations thereof; the substituent(s) each being bonded to at least one carbon atom of a terminal ring of pentacene (that is, a carbon atom selected from the number 1, 2, 3, 4, 8, 9, 10, and 11 carbon atoms of pentacene) and being the only substituent(s) (that is, hydrogen is bonded to the carbon atoms of the non-terminal rings, as well as to any carbon atom of a terminal ring that does not bear a substituent); with the proviso that when the compound has only two substituents, both of which are methyl or alkoxy, and one substituent is bonded to the number 2 carbon atom, the other substituent, if methyl, is bonded to the number 1, 3, 4, 8, or 11 carbon atom and, if alkoxy, is bonded to the number 1, 3, 4, 8, 9, or 11 carbon atom; and with the further proviso that when the compound has only four substituents, all of which are alkoxy, the substituents are bonded to the numbers 2, 3, 9, and 10 carbon atoms. As used herein, the term "combinations" of substituents includes, monovalent combinations (for example, a bromomethyl substituent) as well as substituents formed by the bonding together of the substituents on two adjacent carbon atoms to form a ring structure (for example, two alkyl substituents on adjacent carbon atoms can be bonded together to form a divalent alkylene group that bridges or links the carbon atoms).

Preferably, each substituent is independently selected from the group consisting of alkyl groups, alkoxy groups, thioalkoxy groups, halogen atoms, and combinations thereof. More preferably, each substituent is independently an alkyl group, an alkoxy group, or a combination thereof. Most preferably, each substituent is independently an alkyl group.

Preferably, the compounds are disubstituted (that is, the compounds have only two substituents). More preferably, the compounds are disubstituted in a manner such that the substituents are bonded to different terminal rings. Even more preferably, the compounds are disubstituted with the substituents being bonded to the numbers 2 and 9 carbon atoms or the numbers 2 and 10 carbon atoms. Most preferably, the compounds are disubstituted with the substituents being bonded to the numbers 2 and 9 carbon atoms.

The above-described substituted pentacene compounds of the invention (having at least one non-hydrogen substituent) include those which can be represented by the following general formula:

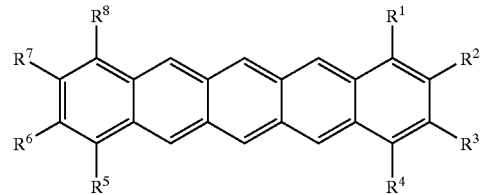

Formula II wherein each R (that is, each of the groups $R^1$ through $R^8$) is independently selected from the group consisting of electron-donating groups, halogen atoms, hydrogen atoms, and combinations thereof (with the proviso, as indicated above, that the class excludes 2,9-dimethylpentacene, 2,10-dimethylpentacene, 2,10-dialkoxypentacenes, and 1,4,8,11-tetraalkoxypentacenes). Preferably, each R is independently selected from the group consisting of alkyl groups, alkoxy groups, thioalkoxy groups, halogen atoms, hydrogen atoms, and combinations thereof. More preferably, each R is independently selected from the group consisting of alkyl groups, alkoxy groups, hydrogen atoms, and combinations thereof. Even more preferably, each R is independently an alkyl group or a hydrogen atom. Most preferably, each R is independently methyl, n-hexyl, n-nonyl, n-dodecyl, sec-butyl, 3,5,5-trimethylhexyl, 2-ethylhexyl, or a hydrogen atom.

Preferably, only $R^2$ and $R^6$ (or $R^2$ and $R^7$) are moieties other than hydrogen. That is, preferably, $R^2$ and $R^6$ (or $R^2$ and $R^7$) are independently selected from the group consisting of electron-donating groups, halogen atoms, and combinations thereof, and $R^1$, $R^3$, $R^4$, $R^5$, $R^7$, and $R^8$ (or $R^1$, $R^3$, $R^4$, $R^5$, $R^6$, and $R^8$) are hydrogen. More preferably, $R^2$ and $R^6$ (or $R^2$ and $R^7$) are independently selected from the group consisting of alkyl groups, alkoxy groups, thioalkoxy groups, halogen atoms, and combinations thereof, and $R^1$, $R^3$, $R^4$, $R^5$, $R^7$, and $R^8$ (or $R^1$, $R^3$, $R^4$, $R^5$, $R^6$, and $R^8$) are hydrogen. Still more preferably, $R^2$ and $R^6$ (or $R^2$ and $R^7$) are independently selected from the group consisting of alkyl groups, alkoxy groups, and combinations thereof, and $R^1$, $R^3$, $R^4$, $R^5$, $R^7$, and $R^8$ (or $R^1$, $R^3$, $R^4$, $R^5$, $R^6$, and $R^8$) are hydrogen. Even more preferably, $R^2$ and $R^6$ (or $R^2$ and $R^7$) are independently alkyl, and $R^1$, $R^3$, $R^4$, $R^5$, $R^7$, and $R^8$ (or $R^1$, $R^3$, $R^4$, $R^5$, $R^6$, and $R^8$) are hydrogen. Most preferably, $R^2$ and $R^6$ (or $R^2$ and $R^7$) are independently selected from the group consisting of methyl groups, n-hexyl groups, n-nonyl groups, n-dodecyl groups, sec-butyl groups, 3,5,5-trimethylhexyl groups, 2-ethylhexyl groups, and $R^1$, $R^3$, $R^4$, $R^5$, $R^7$, and $R^8$ (or $R^1$, $R^3$, $R^4$, $R^5$, $R^6$, and $R^8$) are hydrogen.

Representative examples of the compounds of the invention include:

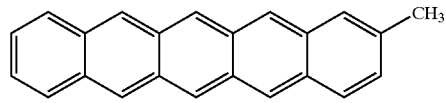

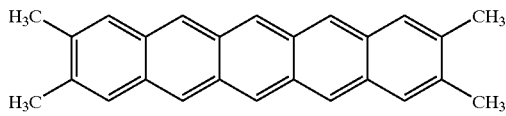

-continued
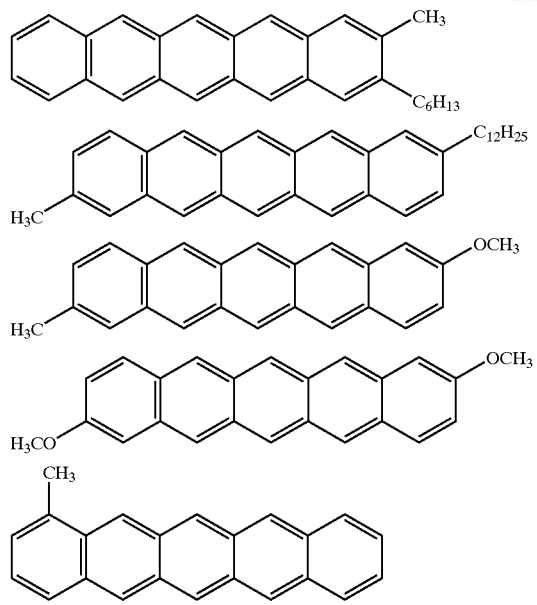
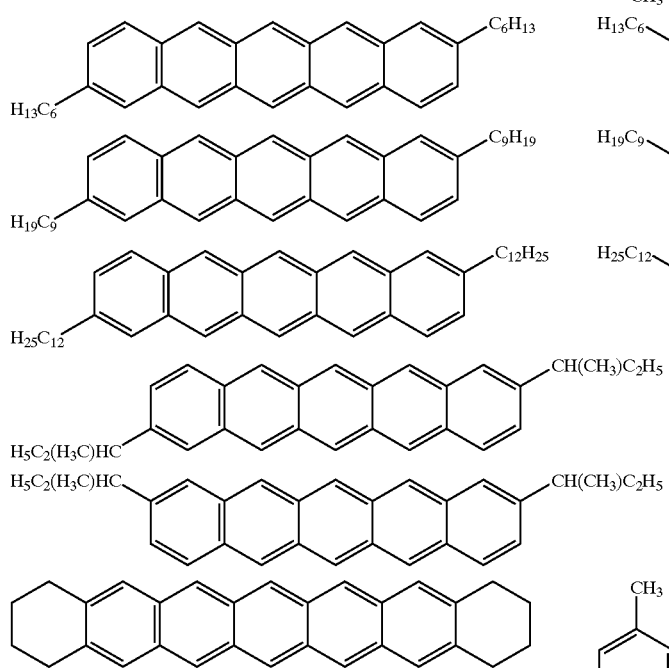
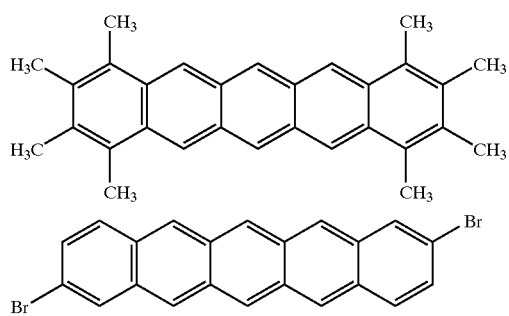
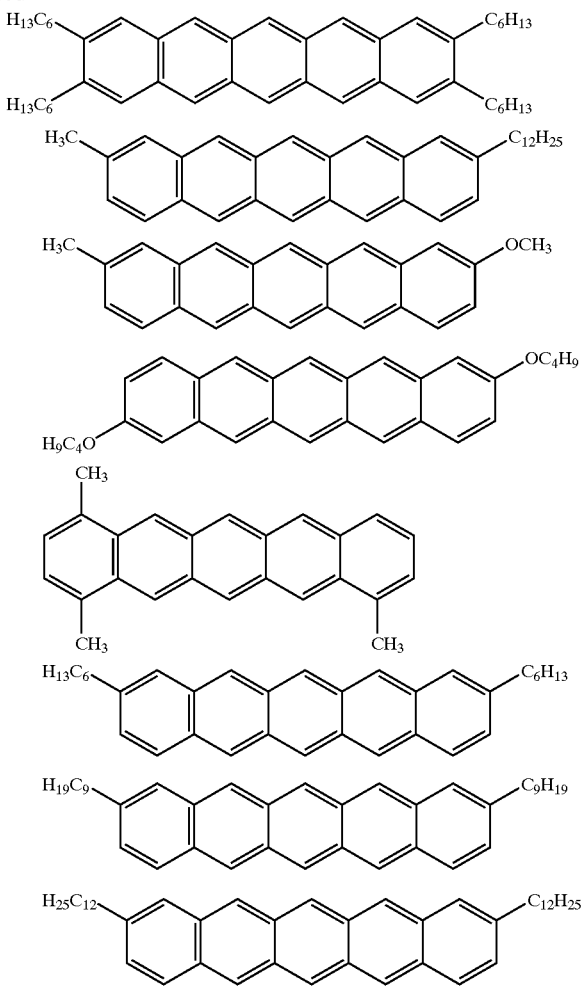
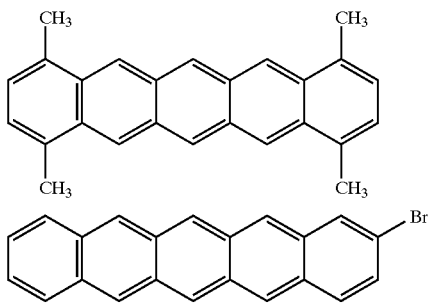
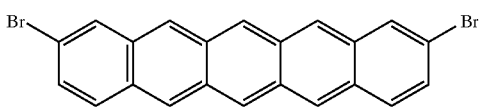

-continued
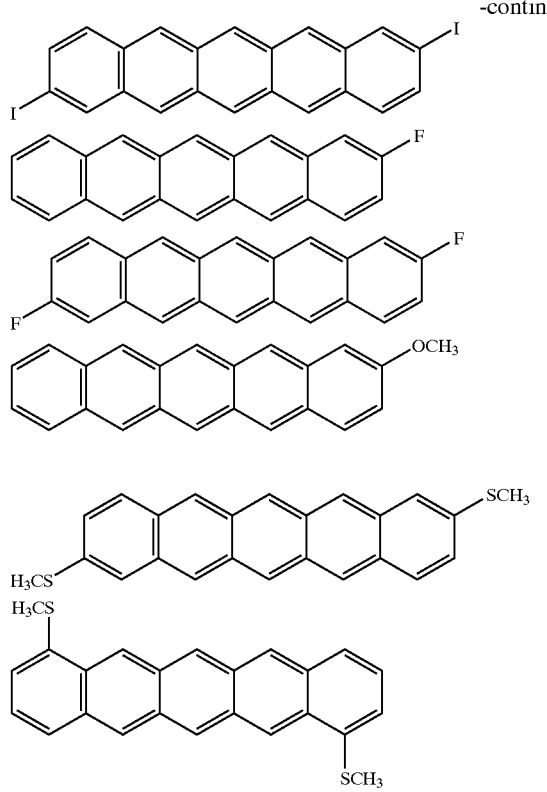
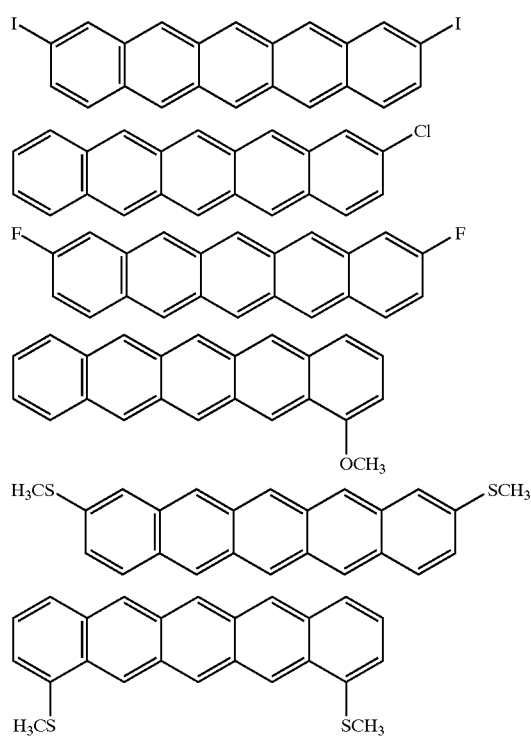
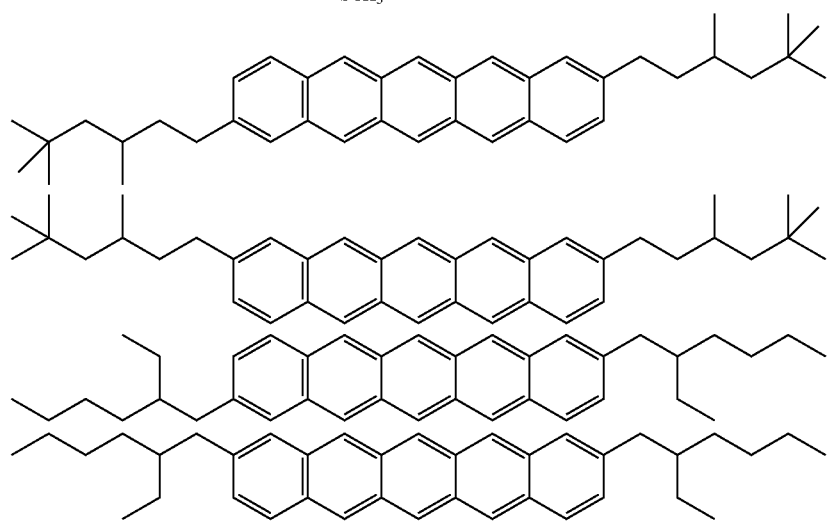
Preferred compounds include, for example:
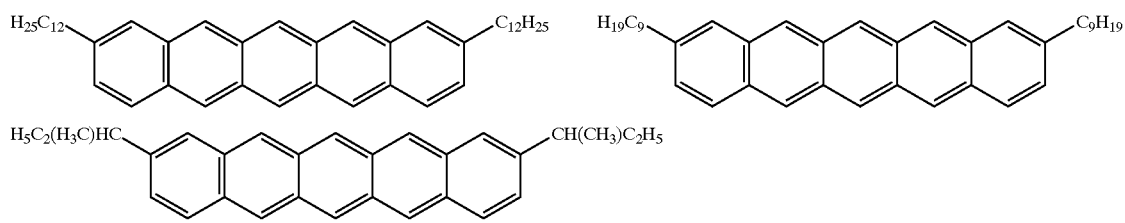

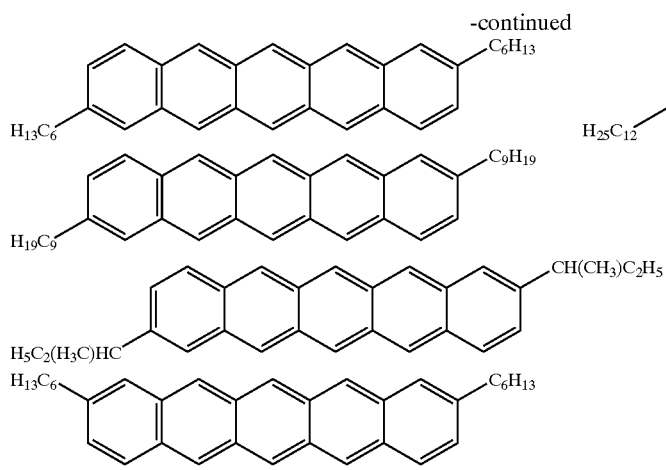
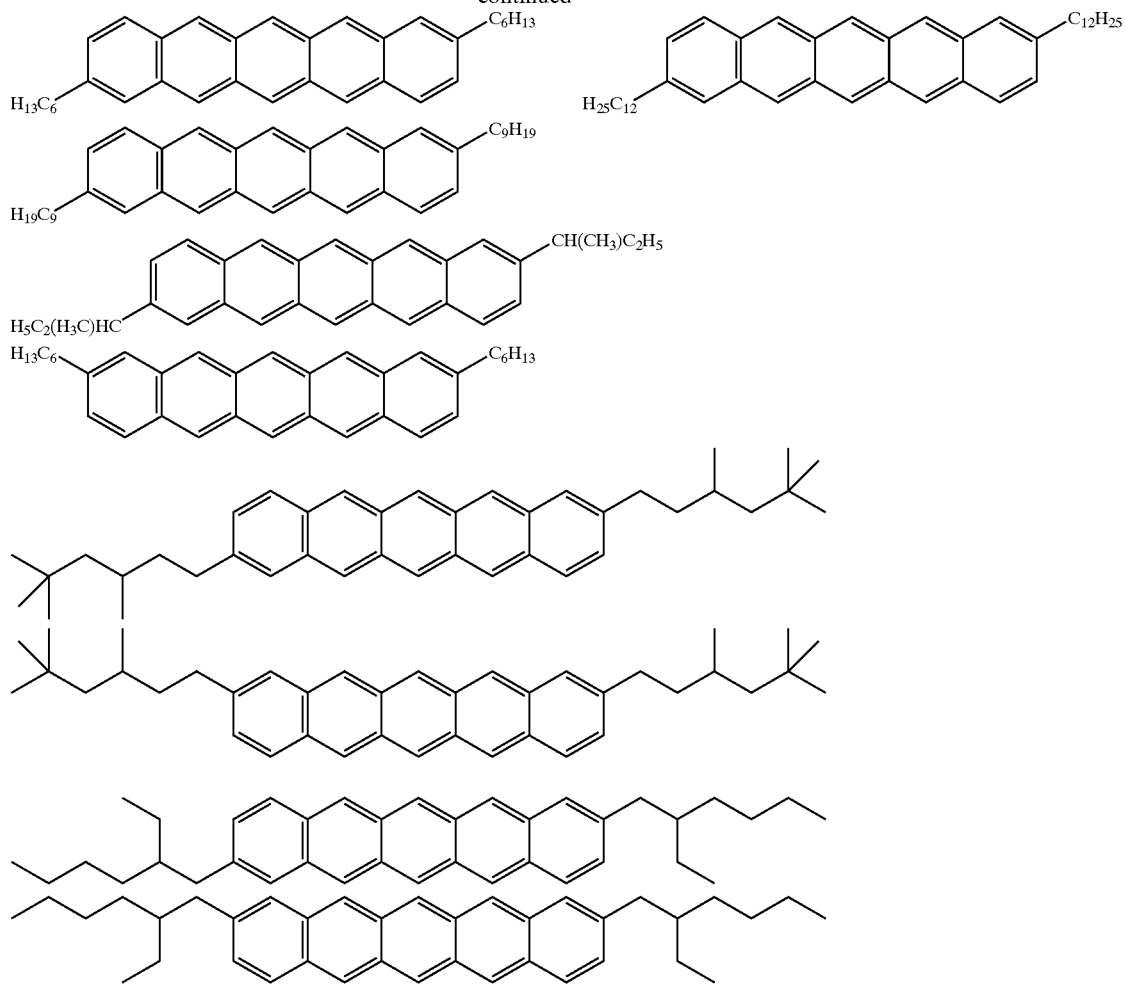
More preferred compounds include, for example:
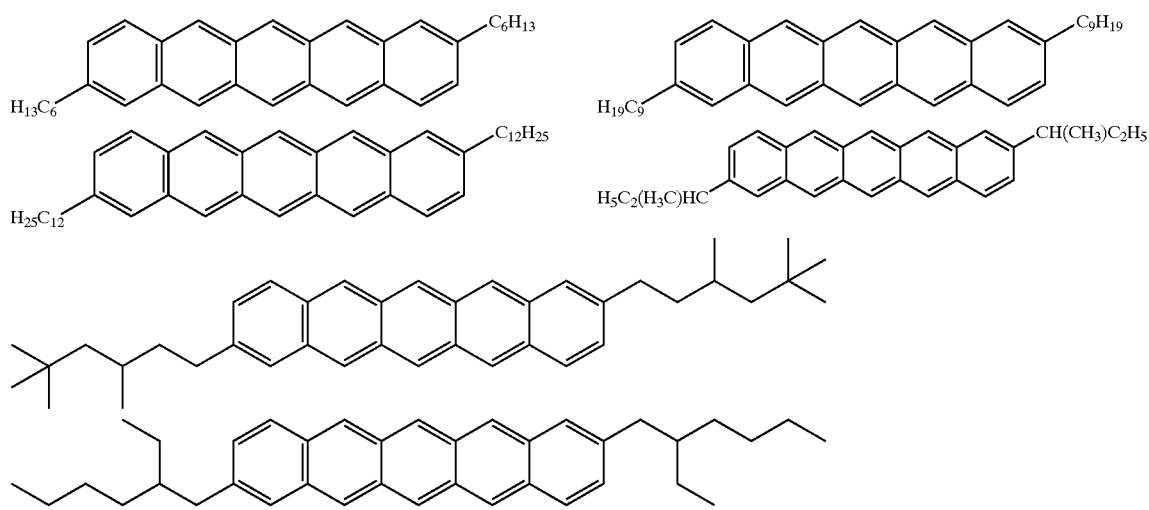
Preparation of Compounds
The compounds of the invention (as well as 2,9-dimethylpentacene, 2,10-dimethylpentacene, 2,10-dialkoxypentacenes, and 1,4,8,11-tetraalkoxypentacenes) can be prepared by a process comprising the steps of (1) combining at least one substituted benzene (more specifically, at least one mono-, di-, tri-, or tetrasubstituted benzene having at least two adjacent ring carbon atoms that are bonded to hydrogen) and pyromellitic dianhydride (or a derivative thereof), in the presence of a Lewis acid (for example, AlCl$_3$), to form substituted bis(benzoyl)phthalic acids via a Friedel-Crafts reaction; (2) reducing the substituted bis(benzoyl)phthalic acids to give the corresponding substituted bis(benzyl)phthalic acids; (3) cyclizing the substituted bis(benzyl)phthalic acids to give the corresponding substituted pentacenediones; (4) reducing the substituted pentacenediones to give the corresponding substituted pentacenediols; and (5) dehydrating the substituted pentacenediols to form the corresponding substituted pentacenes. (As used herein, the term "phthalic acid" refers to terephthalic acid (1,4-benzenedicarboxylic acid) and isophthalic acid (1,3-benzenedicarboxylic acid) collectively.)

The step of combining at least one substituted benzene with pyromellitic dianhydride (benzene-1,2,4,5-tetracarboxylic acid dianhydride) or a derivative thereof (for example, dimethyl 2,5-bis(chlorocarbonyl)terephthalate) to form substituted bis(benzoyl)phthalic acids can be represented by the following general scheme:

Reaction Scheme A

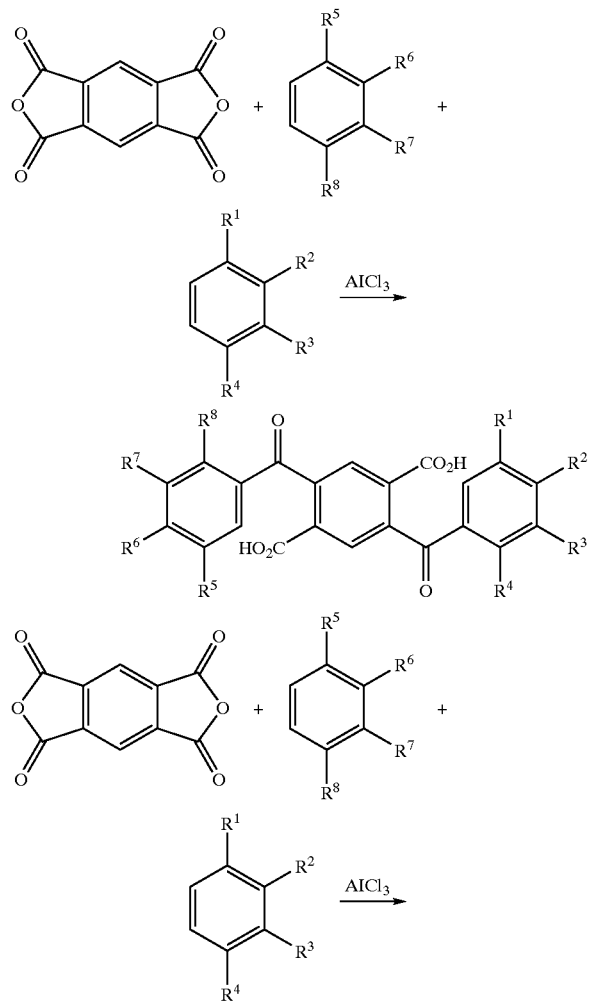

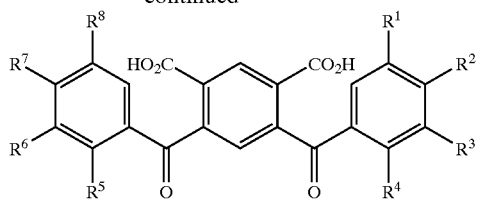

wherein each R (that is, each of the groups $R^1$ through $R^8$) is defined as above for Formula II, with the clarification that preferably $R^2$ and $R^6$ are moieties other than hydrogen for the substituted bis(benzoyl)terephthalic acid (and that $R^2$ and $R^7$ are moieties other than hydrogen for the substituted bis(benzoyl)isophthalic acid).

Reactions of this type (electrophilic aromatic substitution reactions) are well known in organic chemistry and have been described, for example, by Henri de Diesbach and Victor Schmidt in Helv. Chim. Acta 7, 648 (1924); by William Hobson Mills and Mildred Mills in J. Chem. Soc. 101, 2200 (1912); by Ernst Philippi in Monatshefte fuer Chemie 32, 634 (1911); by Ernst Philippi and Reinhard Seka in Monatshefte fuer Chemie 43, 615 (1922); by Ernst Philippi and Fedora Auslaender in Monatshefte fuer Chemie 42, 1 (1921); and by Guido Machek in Monatshefte fuer Chemie 56, 130 (1930).

Preferably, the reaction is carried out in the presence of an inert solvent and an amine base in order to keep the reaction mixture fluid and to decrease the amount of rearrangement of the substituents on the aromatic ring during the reaction. Examples of useful inert solvents include 1,2-dichloroethane, dichlorobenzene, dichloromethane, carbon disulfide, nitrobenzene, and nitromethane. Examples of useful amine bases include tertiary amines such as triethylamine, diisopropylethylamine, and 1,4-diazabicyclo[2.2.2]octane (DABCO). If desired, the reaction mixture can be agitated and/or heated.

Representative examples of substituted benzenes that can be used to prepare the substituted bis(benzoyl)phthalic acids include mono- and dialkoxybenzenes; mono- and dithioalkoxybenzenes; mono- and dihalobenzenes; and mono-, di-, tri-, and tetraalkylbenzenes (for example, toluene, hexylbenzene, nonylbenzene, dodecylbenzene, sec-butylbenzene, p-xylene, 1,2,3,4-tetrahydronaphthalene, 3,5,5-trimethylhexylbenzene, 2-ethylhexylbenzene, and 1,2,3,4-tetramethylbenzene).

Alternatively, the substituted bis(benzoyl)phthalic acids can be prepared by reaction of pyromellitic dianhydride or a derivative thereof with a substituted aromatic organometallic reagent (for example, an aryl magnesium halide or an aryl lithium compound).

The resulting substituted bis(benzoyl)phthalic acids can be reduced to the corresponding substituted bis(benzyl)phthalic acids via reduction methods known in the art. For example, the reduction can be accomplished by using either zinc and aqueous ammonium hydroxide (preferably, with agitation) or catalytic hydrogenation with, for example, palladium or platinum on carbon at, for example, about 2 to 3 atmospheres (preferably, by catalytic hydrogenation; more preferably, by catalytic hydrogenation with palladium on carbon) as shown, for example, below:

Reaction Scheme B

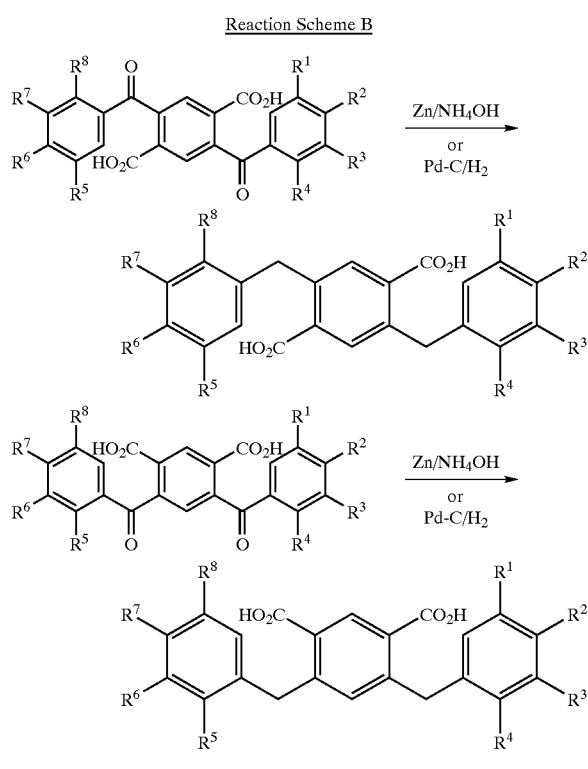

wherein each R (that is, each of the groups $R^1$ through $R^8$) is as defined above for Scheme A. If desired, the substituted bis(benzoyl)terephthalic acids can be separated from the substituted bis(benzoyl)isophthalic acids by methods commonly used in the art (for example, by recrystallization, trituration, or chromatography) before the reduction reaction is carried out (or, alternatively, the resulting substituted bis(benzyl)phthalic acid isomers can be separated thereafter).

The cyclization step of the process can be accomplished via intramolecular Friedel-Crafts cyclization of the substituted bis(benzyl)phthalic acids to form the corresponding substituted pentacenediones (the substituted 7,14-dihydropentacene-5,12-diones and the substituted pentacene-5,7(12H,14H)-diones; hereinafter, the "5,12-diones" and the "5,7-diones").

The use of acid catalyzed Friedel-Crafts cyclization to form cyclic ketones is well known in the literature and has been described, for example, by Premasagar et al. in J. Org. Chem., 46(14), 2974 (1981); by Allen et al. in Tetrahedron, 33(16), 2083 (1977); and by Hulin et al. in J. Org. Chem., 49, 207 (1984). These reactions can generally be carried out at about 0° C. to 100° C. in the presence of a strong acid such as concentrated sulfuric acid, fuming sulfuric acid, polyphosphoric acid or anhydrous hydrofluoric acid. For example, unsubstituted bis(benzoyl)phthalic acid will form the corresponding tetrone when heated to 100° C. with concentrated sulfuric acid for several hours.

However, both substituted bis(benzoyl)phthalic acids and substituted bis(benzyl)phthalic acids are usually unreactive under these conditions. It appears that in general the intramolecular Friedel-Crafts cyclization of these substituted compounds cannot be readily accomplished with the strong acids that are typically used for this type of reaction. It has been discovered, however, that Friedel-Crafts cyclization of substituted bis(benzyl)phthalic acids to form the corresponding substituted pentacenediones can be accomplished using an acid composition comprising trifluoromethanesulfonic acid as shown, for example, below:

Reaction Scheme C

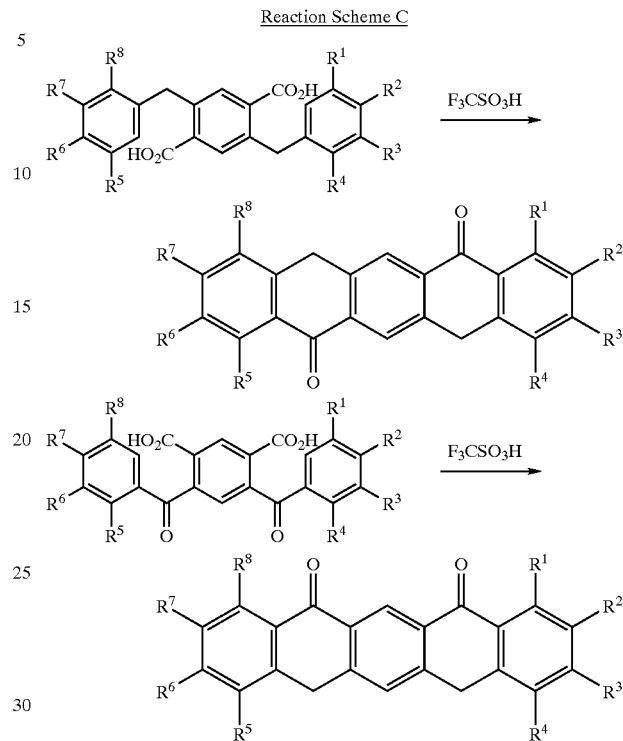

wherein each R (that is, each of the groups $R^1$ through $R^8$) is defined as above for Formula II, with the clarification that preferably $R^2$ and $R^6$ are moieties other than hydrogen for the substituted 5,12-dione (and that $R^2$ and $R^7$ are moieties other than hydrogen for the substituted 5,7-dione).

The cyclization reaction can be carried out at room temperature or, optionally, at elevated temperatures (for example, a temperature in the range of about 20° C. to 60° C.) and, preferably, with agitation of the reaction mixture. The trifluoromethanesulfonic acid can be used alone or in combination with, for example, trifluoroacetic acid, or a perfluoroalkanesulfonic acid of higher molecular weight than trifluoromethanesulfonic acid, or a neutral solvent that will not react with trifluoromethanesulfonic acid (for example, a hydrocarbon solvent, a chlorinated solvent such as methylene chloride or a fluorinated solvent) or a Lewis acid (for example, antimony pentafluoride).

The resulting substituted pentacenediones can be reduced and dehydrated to give the corresponding substituted pentacenes. Good yields can usually be obtained by, for example, a sodium borohydride reduction procedure, as shown, for example, below:

Reaction Scheme D

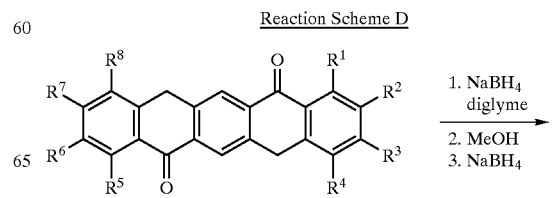

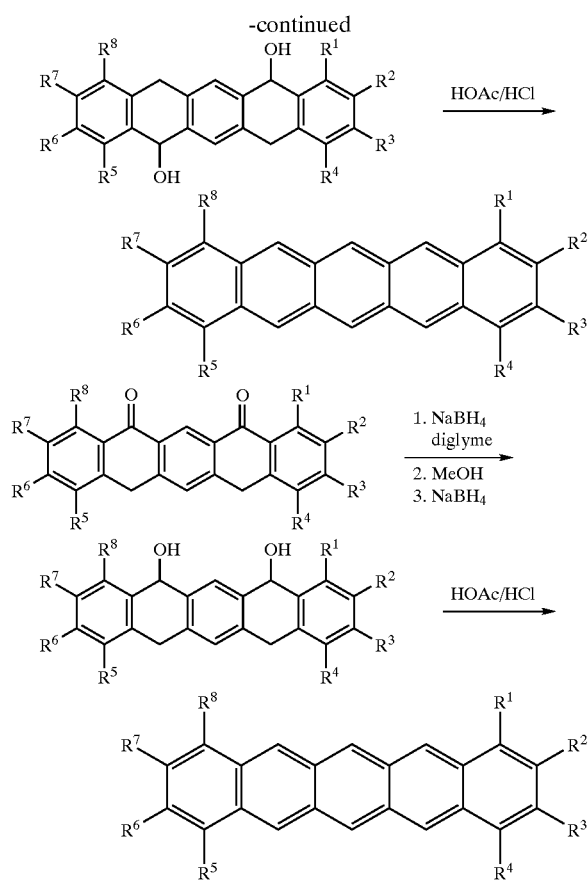

wherein each R (that is, each of the groups R¹ through R⁸) is defined as above for Reaction Scheme C.

Treatment of the diones with sodium borohydride in solvent, such as alcohol(s) or ether(s) (preferably, diglyme) or a combination thereof, preferably followed by addition of methanol and then treatment with additional sodium borohydride gives the corresponding substituted diols. The diols can then be dehydrated to substituted pentacenes by treatment with an acid (for example, hydrochloric acid), preferably with application of heat (for example, heating to about 50° C. to 60° C.) and agitation. Suitable acids include, for example, acetic acid, phosphoric acid, hydrochloric acid, sulfuric acid, hydroiodic acid, hydrobromic acid, trifluoroacetic acid, and trifluoromethanesulfonic acid. Optionally, the diols can first be treated with a weak acid, such as acetic acid, followed by treatment with a stronger acid, such as hydrochloric acid.

If desired, the resulting substituted pentacenes can be purified one or more times by standard methods such as recrystallization, sublimation, or a combination thereof. Purification can be accomplished by sublimation, for example, using a 3-zone furnace (for example, a Thermolyne 79500 tube furnace, available from Barnstead Thermolyne, Dubuque, Iowa) at reduced pressure under a constant flow of nitrogen gas.

Semiconductor Devices

The compounds of the invention and also 2,9-dimethylpentacene, 2,10-dimethylpentacene, 2,10-dialkoxypentacenes, and 1,4,8,11-tetraalkoxypentacenes can be used as the semiconductor layer in semiconductor devices. There are numerous types of semiconductor devices. Common to all is the presence of one or more semiconductor materials. Semiconductor devices have been described, for example, by S. M. Sze in *Physics of Semiconductor Devices*, 2$^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes), photoconductors, current limiters, thermistors, p-n junctions, field-effect diodes, Schottky diodes, and so forth. In each semiconductor device, the semiconductor material is combined with one or more metals or insulators to form the device. Semiconductor devices can be prepared or manufactured by known methods such as, for example, those described by Peter Van Zant in *Microchip Fabrication*, Fourth Edition, McGraw-Hill, New York (2000).

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, *Physics of Semiconductor Devices*, 2$^{nd}$ edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

The substituted pentacene compounds of the invention and 2,9-dimethylpentacene, 2,10-dimethylpentacene, 2,10-dialkoxypentacenes, and 1,4,8,11-tetraalkoxypentacenes can be used alone or in combination as the organic semiconductor layer of the OTFT (or other semiconductor device). The layer can be provided by any useful means, such as, for example, vapor deposition and printing techniques. Some of the compounds of the invention (for example, those bearing two nonyl, hexyl, or sec-butyl substituents) are at least somewhat soluble in organic solvents and can be solution deposited (for example, by spin coating, dip coating, ink jet printing, casting, or other known techniques).

The substituted pentacene compounds of the invention, 2,9-dimethylpentacene, 2,10-dimethylpentacene, 2,10-dialkoxypentacenes, and 1,4,8,11-tetraalkoxypentacenes can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

EXAMPLES

Objects and advantages of this invention are further illustrated by the following examples, but the particular materials and amounts thereof recited in these examples, as well as other conditions and details, should not be construed to unduly limit this invention.

Unless otherwise specified, all starting materials were obtained from Aldrich, Milwaukee, Wis. 2,5-Bis(4-methylbenzoyl)terephthalic and 4,6-bis(4-methylbenzoyl)isophthalic acids were prepared essentially essentially as described in H. de Diesbach, V. Schmidt, Helv. Chim. Acta, 7, 648 (1924). 2,5-Dibenzoylterephthalic acid and 4,6-dibenzoylisophthalic acid were prepared as described in W. Hobbson, M. Mills, J. Chem. Soc. 101, 2200 (1912).

Example 1

Preparation of 2,9-Dihexylpentacene
Preparation of 2,5-Bis(4-hexylbenzoyl)terephthalic Acid To a mixture of 25.7 grams of aluminum chloride, 51.3 mL of 1,2-dichloroethane, and 10 grams of benzene-1,2,4,5-tetracarboxylic acid dianhydride (pyromellitic dianhydride) was added with cooling, a solution of 14.9 grams of hexylbenzene and 6.40 grams of diisopropylethylamine in 25 mL of 1,2-dichloroethane over a period of 3.5 hours, keeping the temperature between 15° C. and 20° C. The resulting mixture was stirred for an additional 15 minutes after the addition was complete, and it was then heated to 40° C. for one hour. The warm mixture was poured into a beaker with 200 grams of ice and 75 mL of concentrated hydrochloric acid and stirred overnight at room temperature. The aqueous phase was poured off and the resulting oily solid was stirred with 500 mL of water, and the water was poured off. This water wash was repeated, and the resulting residue was dissolved in 250 mL of acetone and concentrated in vacuo. This residue was stirred with 55 mL of ethyl acetate, and the resulting solid was collected by filtration, washed with 100 mL of ethyl acetate, and dried to give 2,5-bis(4-hexylbenzoyl)terephthalic acid.

Preparation of 2,5-Bis(4-hexylbenzyl)terephthalic Acid

A mixture of 5.26 grams of 2,5-bis(4-hexylbenzoyl)terephthalic acid, 100 mL of tetrahydrofuran, and 0.53 grams of 5% palladium on carbon (as a catalyst) was heated at 65° C. for 17 hours in an atmosphere of hydrogen at 270 kPa. The resulting mixture was filtered through Celite™ diatomaceous earth filter agent to remove the catalyst. The filtrate was concentrated in vacuo to give 2,5-bis(4-hexylbenzyl)terephthalic acid.

Preparation of 3,10-Dihexyl-7,14-dihydropentacene-5,12-dione

A mixture of 2.56 grams of 2,5-bis(4-hexylbenzyl)terephthalic acid, 25.6 grams of trifluoroacetic acid, and 12.8 gram of trifluoromethanesulfonic acid was stirred overnight at room temperature. The resulting mixture was poured over 200 grams of ice. The solid was collected by filtration and washed with saturated aqueous sodium bicarbonate solution and then with 400 mL of water until the filtrate was neutral to pH paper. The solid was dried to give 3,10-dihexyl-7,14-dihydropentacene-5,12-dione.

Preparation of 2,9-Dihexylpentacene

A mixture of 20 grams of 3,10-dihexyl-7,14-dihydropentacene-5,12-dione and 200 mL of 2-methoxyethyl ether was stirred and flushed with nitrogen for 15 minutes. To this was added 13.4 grams of sodium borohydride, and stirring was continued at room temperature overnight. To the resulting mixture was added 126 mL of methanol over 1.25 hours. The temperature increased to 40° C. and was maintained at 40° C. during the addition by intermittent application of a cold water bath. When addition was complete stirring was continued at room temperature. After stirring for 2 hours at room temperature an additional 50 mL of 2-methoxyethyl ether was added. After stirring with methanol for a total of 3.5 hours, 300 mL of acetic acid was added, and the resulting mixture was heated to 60° C. for 1.5 hours. To the mixture was added 100 mL of concentrated hydrochloric acid and heating at 60° C. was continued for one hour. The mixture was cooled to room temperature and the resulting solid was collected by filtration and washed with 500 mL of water. The solid was washed with 500 mL of acetone and then 60 mL of tetrahydrofuran. The solid was washed with an additional one liter of acetone and dried to give 2,9-dihexylpentacene.

Example 2

Preparation of 2,9-Dinonylpentacene
Preparation of 2,5-Bis(4-nonylbenzoyl)terephthalic Acid To a mixture of 1370 grams of aluminum chloride, 533.7 grams of benzene-1,2,4,5-tetracarboxylic acid dianhydride and 2750 mL of 1,2-dichloroethane stirred at 15° C. was added a solution of 341.5 grams of N,N-diisopropylethylamine in 1334 mL of 1,2-dichloroethane over a period of 3.5 hr, keeping the reaction temperature between 15° C. and 20° C. The resulting reaction mixture was stirred overnight at room temperature. The reaction mixture was added to a mixture of 2500 grams of ice and 2500 mL of concentrated hydrochloric acid with efficient stirring. The mixture was divided into 800 mL portions and each portion was worked up as follows. To 800 mL of the mixture was added 800 mL of tetrahydrofuran, 800 mL of ethyl acetate and 800 mL of water. The mixture was stirred and phase split. The organic phase was filtered and the filtrate was concentrated in vacuo. The residues were combined. To 711 grams of the combined residue was added 4 L of acetone and the mixture was stirred until a suspension of a fine solid resulted. The solid was collected by filtration and washed with 1 L of acetone. The solid was dried to give 2,5-bis(4-nonylbenzoyl)terephthalic acid.

Preparation of 2,5-Bis(4-nonylbenzyl)terephthalic Acid

A mixture of 109 grams of 2,5-bis(4-nonylbenzoyl) terephthalic acid 1500 mL of tetrahydrofuran, and 7.43 grams of 10% palladium on carbon (as a catayst)was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give 2,5-bis(4-nonylbenzyl)terephthalic acid.

Preparation of 7,14-Dihydro-3,10-dinonylpentacene-5,12-dione

A mixture of 26.3 grams of 2,5-bis(4-nonylbenzyl) terephthalic acid and 100 mL of trifluoromethanesulfonic acid was heated to 60° C. and maintained for one hour. The mixture was cooled to room temperature and poured over 500 grams of ice. The resulting solid was collected by filtration and washed with one liter of water, two liters of saturated aqueous sodium bicarbonate solution, and four liters of water until the filtrate was neutral to pH paper. The solid was washed with two liters of acetone and dried to give 7,14-dihydro-3,10-dinonylpentacene-5,12-dione.

Preparation of 2,9-Dinonylpentacene

A mixture of 20 grams of 7,14-dihydro-3,10-dinonylpentacene-5,12-dione and 400 mL of 2-methoxyethyl ether was stirred and flushed with nitrogen for 15 minutes. To this was added 11.4 grams of sodium borohydride and stirring was continued at 60° C. for 18 hours. The resulting mixture was cooled to room temperature, 3.0 grams of sodium borohydride was added, and stirring was continued for 16 hours at room temperature. To the resulting mixture was added 170 mL of acetic acid, and the mixture was heated at 60° C. for one hour. To this mixture was added 120 mL of concentrated hydrochloric acid and heating was continued at 60° C. for one hour. The resulting mixture was cooled to room temperature and the solid was collected by filtration and dried to give 2,9-dinonylpentacene.

Example 3

Preparation of 2,9-Didodecylpentacene

Preparation of 2,5-Bis(4-dodecylbenzoyl)terephthalic Acid

To a mixture of 492 grams of aluminum chloride and 988 mL of 1,2-dichloroethane was added 192 grams of benzene-1,2,4,5-tetracarboxylic acid dianhydride (pyromellitic dianhydride). The resulting mixture was cooled to 16° C. and a solution of 434 grams of 1-dodecylbenzene, 123 grams of diisopropylethylamine and 480 mL of 1,2-dichloroethane was added over a period of 3.5 hours, keeping the temperature between 15° C. and 20° C. during the addition. The mixture was stirred overnight at room temperature and poured into a beaker of 1000 grams of ice and 1000 grams concentrated hydrochloric acid. The mixture was stirred for one hour and the liquid was poured from the coagulate. The mixture was divided into 800 mL portions and each portion was worked up as follows. To 800 mL of the mixture was added 800 mL of tetrahydrofuran, 800 mL of ethyl acetate, and 800 mL of water. The mixture was stirred and phase split. The organic phase was filtered and the filtrate was concentrated in vacuo. The residues were combined. To 127 grams of the combined residue was added 800 mL of ethyl acetate and the mixture was stirred until a suspension of a fine solid resulted. The solid was collected by filtration and washed with 50 mL of ethyl acetate. The solid was dried to give 2,5-bis(4-dodecylbenzoyl)terephthalic acid.

Preparation of 2,5-Bis(4-dodecylbenzyl)terephthalic Acid

A solution of 133 grams of 2,5-bis(4-dodecylbenzoyl) terephthalic acid and 1 L of tetrahydrofuran was treated with 8 grams of 10% palladium on carbon (as a catalyst) and heated to 65° C. for 17 hours in an atmosphere of hydrogen at 270 kPa. The reaction mixture was filtered through Celite™ diatomaceous earth filter agent to remove the catalyst. The filtrate was concentrated in vacuo to give a white solid. The solid was triturated with ethyl acetate, and the residue was dried to give 2,5-bis(4-dodecylbenzyl) terephthalic acid.

Preparation of 3,10-Didodecyl-7,14-dihydropentacene-5,12-dione

A mixture of 22.7 grams of 2,5-bis(4-dodecylbenzyl) terephthalic acid and 80 mL of trifluoromethanesulfonic acid was heated to 60° C. for one hour. The mixture was cooled to room temperature and poured over 500 grams of ice. The resulting precipitate was collected by filtration and washed with one liter of water, two liters of saturated aqueous sodium bicarbonate solution, and four liters of water until the filtrate was neutral to pH paper. The solid was washed with two liters of acetone and dried to give 3,10-didodecyl-7,14-dihydropentacene-5,12-dione.

Preparation of 2,9-Didodecylpentacene

A mixture of 8.5 grams of 3,10-didodecyl-7,14-dihydropentacene-5,12-dione and 250 mL of 2-methoxyethyl ether was stirred and flushed with nitrogen for 15 minutes. To this was added 4.46 grams of sodium borohydride. The resulting mixture was heated to 60° C. for 18 hours. The mixture was cooled to room temperature, and 42 mL of methanol was added slowly. The resulting mixture was stirred at room temperature for 30 minutes. To this was added 1.2 grams of sodium borohydride, and stirring was continued at room temperature for 16 hours. To the resulting mixture was added 60 mL of acetic acid, and the mixture was heated at 60° C. for one hour. To this mixture was added 43 mL of concentrated hydrochloric acid, and heating was continued at 60° C. for one hour. To the resulting mixture was added 100 mL of water and the mixture cooled to room temperature and the solid was collected by filtration and dried to give 2,9-didodecylpentacene.

Example 4

Preparation of 1,2,3,4,10,11,12,13-Octahydroheptacene

Preparation of 2,5-Bis(5,6,7,8-tetrahydronaphthalene-2-carbonyl)terephthalic Acid and 4,6-Bis(5,6,7,8-tetrahydronaphthalene-2-carbonyl)isophthalic Acid A mixture of 250 grams of aluminum chloride, 500 mL of 1,2-dichloroethane, and 97.4 grams of benzene-1,2,4,5-tetracarboxylic acid dianhydride (pyromellitic dianhydride) was cooled to 15° C. and a solution of 124.1 grams of 1,2,3,4-tetrahydronaphthalene, 48.79 grams of triethylamine, and 243 mL of 1,2-dichloroethane was added slowly dropwise over a period of 1.5 hours keeping the temperature between 15–20° C., followed by stirring overnight at room temperature. The resulting mixture was poured into 1600 grams of ice and 400 grams of concentrated hydrochloric acid and stirred for 20 minutes at room temperature. The top aqueous layer was poured off, and the remaining mixture was diluted with 2 L of ethyl acetate and stirred until a homogeneous solution resulted. The resulting mixture was phase split, and the organic phase was filtered. The organic phase was washed with 600 mL of brine, dried over magnesium sulfate, filtered, and concentrated in vacuo. To the residue was added 500 mL of isopropyl acetate and the resulting mixture was stirred at room temperature. The resulting residue was treated with additional isopropyl acetate and heptane to crystallize the product. The solid product was isolated, washed with heptane, and dried to give a mixture of 2,5-bis(5,6,7,8-tetrahydronaphthalene-2-carbonyl)terephthalic acid and 4,6-bis(5,6,7,8-tetrahydronaphthalene-2-carbonyl)isophthalic acid.

Preparation of 2,5-Bis(5,6,7,8-tetrahydronaphthalen-2-ylmethyl)terephthalic Acid and 4,6-Bis(5,6,7,8-tetrahydronaphthalen-2-ylmethyl)isophthalic Acid A mixture of 94.7 grams of 2,5-bis(5,6,7,8-tetrahydronaphthalene-2-carbonyl)terephthalic acid and 4,6-bis(5,6,7,8-tetrahydronaphthalene-2-carbonyl)isophthalic acid, 1 L of tetrahydrofuran, and 6 grams of 10% palladium on carbon (as a catalyst) was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give a solid. The solid was triturated with ethyl acetate, collected by filtration, and dried to give a mixture of 2,5-bis(5,6,7,8-tetrahydronaphthalen-2-ylmethyl)terephthalic acid and 4,6-bis(5,6,7,8-tetrahydronaphthalen-2-ylmethyl)isophthalic acid Preparation of 1,2,3,4,8,10,11,12,13,17-Decahydroheptacen-6,15-dione and 1,2,3,4,10,11,12,13-Octahydroheptacen-6,8(15H,17H)-dione To a mixture of 35.3 grams of 2,5-bis(5,6,7,8-tetrahydronaphthalen-2-ylmethyl)terephthalic acid and 4,6-bis(5,6,7,8-tetrahydronaphthalen-2-ylmethyl)isophthalic acid was added 120 grams of trifluoromethanesulfonic acid. The resulting mixture was stirred at room temperature for one hour followed by heating to 60° C. for six hours. The mixture was poured over 500 grams of ice. The resulting solid was isolated by filtration and washed with 500 mL of saturated aqueous sodium bicarbonate solution and then 4 L of water until the filtrate was neutral to pH paper. The solid was dried to give a mixture of 1,2,3,4,8,10,11,12,13,17-decahydroheptacen-6,15-dione and 1,2,3,4,10,11,12,13-octahydroheptacen-6,8(15H,17H)-dione Preparation of 1,2,3,4,10,11,12,13-Octahydroheptacene A mixture of 1.0 gram of 1,2,3,4,8,10,11,12,13,17-decahydroheptacen-6,15-dione and 1,2,3,4,10,11,12,13-octahydroheptacen-6,8(15H,17H)-dione and 20 mL of 2-methoxyethyl ether was stirred and flushed with nitrogen for 15 minutes. To this was added 0.766 grams of sodium borohydride. The resulting mixture was stirred overnight at room temperature. To the mixture was added 7.2 mL of methanol and stirring was continued for 30 minutes. To the resulting mixture was added 0.2 grams of sodium borohydride, and stirring was continued at room temperature for 5 hours. The resulting mixture was heated to 60° C. for one hour. To the mixture was added 11.4 mL of glacial acetic acid and 7.3 mL of concentrated hydrochloric acid. The resulting mixture was heated at 60° C. for one hour. To this mixture was added 20 mL of water and the resulting solid was collected by filtration. The solid was washed with water followed by acetone followed by tetrahydrofuran and dried to give 1,2,3,4,10,11,12,13-octahydroheptacene.

Example 5

Preparation of 2,9-Di-sec-butylpentacene

Preparation of 2,5-Bis(4-sec-butylbenzoyl)terephthalic Acid

A mixture of 417 grams of aluminum chloride, 837 mL of 1,2-dichloroethane, and 162 grams of benzene-1,2,4,5-tetracarboxylic acid dianhydride (pyromellitic anhydride) was stirred and cooled to 16° C. To the mixture was added a solution of 200 grams of sec-butylbenzene, 104 grams of diisopropylethylamine, and 140 mL of 1,2-dichloroethane over a 3.5 hour period, maintaining the reaction temperature between 15° C. and 20° C. The mixture was stirred overnight at room temperature and added slowly to 500 grams of ice and 500 mL of concentrated hydrochloric acid. The resulting mixture was stirred for one hour and the liquid was poured from the coagulate. The coagulate was worked up in 500 mL portions as follows. To 500 mL of the coagulate was added 500 mL of water, 500 mL of ethyl acetate and 500 mL of tetrahydrofuran. The mixture was stirred until the solid dissolved and then phase split. The organic phase was filtered and concentrated in vacuo. To 178 grams of the residue was added 178 mL of ethyl acetate and 1600 mL of heptane, and the mixture was stirred until a suspension of a fine solid formed. The solid was collected by filtration and washed with a mixture of 60 mL of ethyl acetate and 540 mL of heptane. The solid was treated with 982 mL of ethyl acetate and 392 mL of heptane and stirred. The solid was collected by filtration and washed with a mixture of 120 mL of ethyl acetate and 480 mL of heptane. The solid was dried to give 2,5-bis(4-sec-butylbenzoyl)terephthalic acid.

Preparation of 2,5-Bis(4-sec-butylbenzyl)terephthalic acid

A mixture of 120 grams of 2,5-bis(4-sec-butylbenzoyl)terephthalic acid, 1.5 L of tetrahydrofuran, and 9.65 grams of 10% palladium on carbon (as a catalyst) was heated at 65° C. for 17 hours in an atmosphere of hydrogen at 270 kPa. The reaction mixture was filtered through Celite™ diatomaceous earth filter agent to remove the catalyst. The filtrate was concentrated in vacuo to give a solid. The solid was triturated with 10% ethyl acetate in heptane, collected and dried to give 2,5-bis(4-sec-butylbenzyl)terephthalic acid.

Preparation of 3,10-Di-sec-butyl-7,14-dihydropentacene-5,12-dione

To five mL of trifluoromethanesulfonic acid was added two grams of 2,5-bis(4-sec-butylbenzyl)terephthalic acid. The temperature was maintained between 16° C. and 25° C. during the addition. The mixture was stirred for five days at room temperature. The mixture was poured over ice and the solid was collected by filtration, and washed with saturated aqueous sodium bicarbonate and then water until the pH of the filtrate was neutral to pH paper. The solid was dried to give 3,10-di-sec-butyl-7,14-dihydropentacene-5,12-dione.

Preparation of 2,9-Di-sec-butylpentacene

A mixture of 2 grams of 3,10-di-sec-butyl-7,14-dihydropentacene-5,12-dione and 45.3 mL of 2-methoxyethyl ether was stirred and flushed with nitrogen for 15 minutes. To this was added 1.52 grams of sodium borohydride and the mixture was heated to 60° C. overnight. The mixture was cooled to room temperature. To the mixture was added 0.4 grams of sodium borohydride and stirring was continued for 30 mintues. To the mixture was added 15 mL of isopropyl alcohol and stirring was continued at room temperature for 5 hours. To the mixture was added 15 mL of methanol. To the mixture was added 1.0 grams of sodium borohydride and stirring was continued at room temperature. To the mixture was added 16 mL of acetic acid and the mixture was heated to 60° C. for one hour. To the mixture was added 16 mL of concentrated hydrochloric acid and heating was continued at 60° C. The resulting solid was collected by filtration and washed with water followed by ethyl acetate and then acetone. The solid was dried to give 2,9-di-sec-butylpentacene.

Example 6

Preparation of 1,4,8,11-Tetramethylpentacene

Preparation of 2,5-Bis(2,5-dimethylbenzoyl)terephthalic Acid

A mixture of 144 grams of benzene-1,2,4,5-tetracarboxylic acid dianhydride (pyromellitic dianhydride), 439 grams of aluminum chloride, and 915 grams of 1,2-dichloroethane was cooled to 15° C. To this was added a mixture of 140 grams of p-xylene, 109 grams of N,N-diisopropylethylamine, and 426 mL of 1,2-dichloroethane over a period of 3.5 hours keeping the temperature between 15° C. and 20° C. The resulting mixture was stirred overnight at room temperature, poured into 2876 grams of ice and 1078 mL concentrated hydrochloric acid and stirred for one hour. The organic layer was washed with 7 L of water. Three liters of water was poured off and the mixture allowed to stand for 4 days, after which the remaining 3 L of water was poured off. To the resulting residue was added 7 L of ethyl acetate and 3 L of tetrahydrofuran. The organic phase was separated and concentrated in vacuo. To 92 grams of the resulting residue was added 1910 mL of ethyl acetate and the mixture was heated to 77° C. for one hour. The mixture was cooled to room temperature and the resulting solid was collected by filtration and dried to give 2,5-bis(2,5-dimethybenzoyl)terephthalic acid.

Preparation of 2,5-Bis(2,5-dimethybenzyl)terephthalic Acid

A mixture of 92 grams of 2,5-bis(2,5-dimethybenzoyl)terephthalic acid in 1.5 L of tetrahydrofuran was treated with 9.2 grams of 10% palladium on carbon (as a catalyst) in an atmosphere of hydrogen at 270 kPa and 65° C. for 17 hours. The reaction mixture was filtered through Celite™ diatomaceous earth filter agent to remove the catalyst. The filtrate was concentrated in vacuo to give a solid. The solid was triturated with ethyl acetate, collected by filtration, and dried. To 75 grams of the solid was added 1250 grams of acetic acid, and the resulting mixture was heated to 117° C. for 30 minutes and cooled to room temperature. The resulting solid was collected by filtration and washed with acetic acid followed by heptane. The resulting residue was dried to give 2,5-bis(2,5-dimethybenzyl)terephthalic acid.

Preparation of 7,14-Dihydro-1,4,8,11-Tetramethylpentacene-5,12-dione

To 200 mL of trifluoromethanesulfonic acid cooled to 18° C. was added slowly 53 grams of 2,5-bis(2,5-dimethylbenzyl)terephthalic acid in small portions as a solid at a rate such that the temperature remained below 25° C. The mixture was allowed to stir for 10 minutes and the cooling bath was removed. The mixture was stirred overnight at room temperature. The mixture was poured over 600 grams of ice and the resulting solid was collected by filtration. The solid was washed with 1 L of water followed by 500 mL of saturated aqueous sodium bicarbonate solution. The solid was washed with water until the pH of the filtrate was neutral to pH paper. The solid was stirred for one hour with 500 mL of tetrahydrofuran and collected by filtration. The solid was washed with tetrahydrofuran and dried to give 7,14-dihydro-1,4,8,11-tetramethylpentacene-5,12-dione.

Preparation of 1,4,8,11-Tetramethylpentacene

A mixture of 1.0 grams of 7,14-dihydro-1,4,8,11-tetramethylpentacene-5,12-dione and 10 mL of 2-methoxyethyl ether was stirred and flushed with nitrogen for 15 minutes. To this was added 0.875 grams of sodium borohydride and stirring was continued at room temperature overnight. To the mixture was added 20 mL of 2-methoxyethyl ether and 0.75 grams of sodium borohydride and heating was continued overnight at 60° C. To the mixture was added 6.3 mL of methanol and 0.75 grams of sodium borohydride and stirring was continued for 6 hours at room temperature. To the mixture was added 15 mL of acetic acid and the mixture was stirred for one hour at room temperature. To the mixture was added 10 mL of concentrated hydrochloric acid and the mixture was heated to 60° C. for 1.5 hours. The solid was isolated by filtration and then washed with water and dried to give 1,4,8,11-tetramethylpentacene.

Example 7

Preparation of 2,9-Di(3,5,5-trimethylhexyl)pentacene

Preparation of 3,5,5-Trimethylhexanoylbenzene

To a mixture of 143.3 grams of aluminum chloride and 400 mL of benzene was added 100 grams of 3,5,5-trimethylhexanoyl chloride over a 50 minute period at a rate such that the temperature did not exceed 35° C. When the addition was complete, the mixture was stirred at room temperature for three hours. The mixture was poured over 500 grams of ice and extracted with 400 mL of ethyl acetate. The organic phase was washed with brine, dried over magnesium sulfate, filtered and the solvent was removed in vacuo to give 3,5,5-trimethylhexanoylbenzene.

Preparation of 3,5,5-Trimethylhexylbenzene

A solution of 116.5 grams of 3,5,5-Trimethylhexanoylbenzene in 1500 mL of tetrahydrofuran with 9.9 grams of 10% palladium on carbon (as a catalyst) was stirred at 23° C. in an atmosphere of hydrogen at 275 kPa for 17 hours. The mixture was filtered through Celite™ diatomaceous earth filter agent to remove the catalyst. The filtrate was concentrated in vacuo to give 3,5,5-trimethylhexylbenzene.

Preparation of 2,5-Bis(4-(3,5,5-trimethylhexyl)benzoyl)terephthalic acid

A mixture of 694.76 grams of aluminum chloride, 270.6 grams of benzene-1,2,4,5-tetracarboxylic acid dianhydride (pyromellitic dianhydride), and 1722.0 grams of 1,2-dichloroethane was stirred at 15° C. A mixture of 507.04 grams of (3,5,5-trimethylhexyl)benzene, 173.17 grams of N,N-diisopropylethylamine and 676.4 mL of 1,2-dichloroethane was added to the reaction over a period of 3.5 hours keeping the reaction temperature between 15° C. and 20° C. The mixture was allowed to stir overnight at room temperature and then added to 1200 g of ice and 1200 mL concentrated hydrochloric acid and stirred for 3 hours. The mixture was extracted with ethyl acetate and the ethyl acetate was washed several times with water. The organic phase was dried with magnesium sulfate and stripped to give a clear thick yellow slurry. To this was added 200 mL ethyl acetate followed by 600 mL of heptane and stirred for 15 minutes. The solid was collected by filtration to give 2,5-bis(4-(3,5,5-trimethylhexyl)benzoyl)terephthalic acid.

Preparation of 2,5-Bis(3,5,5-trimethylhexylbenzyl)terephthalic acid

A mixture containing 20.0 grams of 2,5-bis[4-(3,5,5-trimethylhexyl)benzoyl]terephthalic acid in 1500 mL of tetrahydrofuran (THF) and 1.4 grams of 10% palladium on carbon (as a catalyst) was heated to 90° C. in an atmosphere of hydrogen at 620 kPa and 90° C. for 17 hours. The mixture was filtered through Celite™ diatomaceous earth filter agent to remove the catalyst. The filtrate was concentrated in vacuo to give 2,5-bis[4-(3,5,5-trimethylhexyl)benzyl]terephthalic acid.

Preparation of 7,14-Dihydro-3,10-(3,5,5-trimethylhexyl)pentacene-5,12-dione

A mixture of 16.8 grams of trifluoromethanesulfonic acid and 3.0 grams of 2,5-bis(3,5,5-trimethylhexy)terephthalic acid was stirred for 30 minutes. The reaction temperature was about 30° C. during the addition. The reaction mixture was maintained at 40° C. for 3 hours. The reaction mixture was cooled and poured over ice, filtered and washed with water until the filtrate had a pH of greater than 4. The residue was air dried and then stirred with 200 mL of ethyl acetate. This mixture was filtered and the filtrate was concentrated to give 7,14-Dihydro-3,10-(3,5,5-trimethylhexyl)pentacene-5,12-dione.

Preparation of 2,9-Di(3,5,5-trimethylhexyl)pentacene

To 1 gram of 7,14-dihydro-3,10-(3,5,5-trimethylhexyl)pentacene-5,12-dione in 20 mL of 2-methoxyethyl ether was added 0.56 grams of sodium borohydride. The mixture was stirred and flushed with nitrogen at 100° C. for 2 hours and quenched with 10 mL of methanol at 60° C. over 30 minutes, followed by drop-wise addition of 10 mL of acetic acid and then 5 mL of concentrated hydrochloric acid. The reaction mixture was cooled to room temperature and filtered. A resulting blue solid residue was washed with acetic acid, water, methanol and then finally with acetone and dried. This material was heated in approximately 10 mL of n-butylbenzene and filtered to give 2,9-Di(3,5,5-trimethylhexyl)pentacene.

Example 8

Preparation of 2,9-Di(2-ethylhexyl)pentacene

Preparation of 3,5,5-Trimethylhexanoylbenzene

A mixture of 143.4 grams of aluminum chloride and 351.6 grams of benzene was stirred at room temperature while 100 grams of 3,5,5-trimethylhexanoyl chloride was added to the reaction keeping the reaction temperature at approximately 35° C. over a period of 1.5 hours. The mixture was then stirred for 3 hours. The reaction mixture was poured into 500 grams of ice and stirred until all the ice dissolved. Water was added with cooling to give a homogenous mixture followed by extraction with 400 mL of ethyl acetate. The organic phase was washed with brine, dried with anhydrous magnesium sulfate and stripped to dryness to give 3,5,5-Trimethylhexanoylbenzene.

Preparation of 2-Ethylhexylbenzene

A solution of 313.9 grams of 2-ethylhexanoylbenzene in 500 mL of acetic acid with 11.4 grams of 10% palladium on carbon (as a catalyst) was stirred at 110° C. in an atmosphere of hydrogen at 414 kPa for 34 hours. The mixture was filtered through Celite™ diatomaceous earth filter agent to remove the catalyst. The filtrate was concentrated in vacuo to give 2-ethylhexylbenzene.

Preparation of 2,5-Bis(4-(2-ethylhexyl)benzoyl)terephthalic acid

A mixture of 215.39 grams of aluminum chloride, 83.89 grams of benzene-1,2,4,5-tetracarboxylic acid dianhydride (pyromellitic dianhydride), and 533.85 grams of 1,2-dichloroethane was stirred at 15° C. to 16° C. To this mixture was added a solution of 183 grams of (2-ethylhexyl)benzene and 53.685 grams of N,N-diisopropylethylamine in 198 mL of 1,2-dichloroethane over a period of 3.5 hours keeping the reaction temperature between 15° C. and 20° C. The mixture was stirred overnight at room temperature and then added to 400 g of ice and 400 mL concentrated hydrochloric acid. This mixture was stirred for 1 hour. The mixture was extracted with ethyl acetate. The organic phase was washed with water and brine, dried, and stripped. The resulting solid was stirred with 700 mL ethyl acetate for 10 minutes and 2000 mL of heptane was added. This mixture was stirred for 15 minutes and then filtered. The residue was washed with a mixture of 275 mL ethylacetate/825 mL heptane and air dried to give 2,5-Bis(4-(2-ethylhexyl)benzoyl)terephthalic acid.

Preparation of 2,5-Bis(4-(2-ethylhexyl)benzyl)terephthalic acid

A mixture containing 20.0 grams of 2,5-bis(4-(2-ethylhexyl)benzoyl)terephthalic acid in 1500 mL of THF and 2.9 grams of 10% palladium on carbon (as a catalyst) was heated to 65° C. in an atmosphere of hydrogen at 275 kPa for 17 hours. The mixture was filtered through Celite™ diatomaceous earth filter agent to remove the catalyst. The filtrate was concentrated in vacuo to give 2,5-Bis(4-(2-ethylhexyl)benzyl)terephthalic acid.

Preparation of 3,10-Di(2-ethylhexyl)-7,14-dihydropentacene-5,12-dione

A mixture of 35 grams of 2,5-bis(2-ethylhexy)terephthalic acid and 121 mL of trifluoromethanesulfonic acid was allowed to exotherm to 51° C. The mixture was stirred for a total of 6.5 hours. The mixture was poured over 500 mL of ice and stirred until it was completely mixed. The precipitate was collected and washed with five liters of water until the filtrate had a pH of 4.0. The solid was air dried to give 3,10-Di(2-ethylhexyl)-7,14-dihydropentacene-5,12-dione.

Preparation of 2,9-Di(2-ethylhexyl)pentacene

A method essentially as described above in Example in 7 (Preparation of 2,9-Di(3,5,5-trimethylhexyl)pentacene) is used to prepare 2,9-Di(2-ethylhexyl)pentacene from 3,10-Di(2-ethylhexyl)-7,14-dihydropentacene-5,12-dione

Examples 9–13 and Comparative Examples C1–C3

Preparation of Semiconductor Devices and Testing

Preparation of 2,9-Dimethylpentacene

Preparation of 2,5-Bis(4-methylbenzyl)terephthalic Acid

A mixture of 30.0 grams of 2,5-bis(4-methylbenzoyl) terephthalic acid, 500 mL of acetic acid, and 3 grams of 5% palladium on activated carbon (as a catalyst) was heated to 64° C. for 17 hours in an atmosphere of hydrogen at 270 kPa. The mixture was filtered to remove the catalyst and the product. The catalyst and the product were slurried in 500 mL of tetrahhydrofuran and filtered through Celite™ diatomaceous earth filter agent. The resulting filtrate was concentrated in vacuo. The resulting wet solid was slurried in ethyl acetate and collected by filtration and dried to give 2,5-bis(4-methylbenzyl)terephthalic acid.

Preparation of 7,14-Dihydro-3,10-dimethylpentacene-5,12-dione

To a mixture of 12.7 grams of 2,5-bis(4-methylbenzyl) terephthalic acid and 90 mL of trifluoroacetic acid was added 81.6 grams of trifluoromethanesulfonic acid. The mixture was stirred 22 hours at room temperature. The mixture was poured over 500 grams of ice. The resulting solid precipitate was collected by filtration, and washed with 750 mL of saturated aqueous sodium bicarbonate and then with 1 L of water until the filtrate was neutral to pH paper. The solid was washed with heptane and dried to give 7,14-dihydro-3,10-dimethylpentacene-5,12-dione.

Preparation of 2,9-Dimethylpentacene

A mixture of 24.6 grams of 7,14-dihydro-3,10-dimethylpentacene-5,12-dione in 250 mL of 2-methoxyethyl ether was stirred and flushed with nitrogen for 10 minutes. To this was added in small portions 16.5 grams of sodium borohydride and stirring was continued at room temperature overnight. To the reaction mixture was added slowly over 30 minutes 155 mL of methanol with the temperature maintained below 0° C. The resulting mixture was stirred for 1.5 hours at room temperature. To the mixture was added slowly 360 mL of glacial acetic acid over 10 minutes. The resulting mixture was heated to 60° C. for 1.5 hours. To the mixture was added 100 mL of concentrated hydrochloric acid. The resulting mixture was heated for one hour and cooled to room temperature. To the mixture was added 250 mL of water and stirring was continued for five minutes. The resulting solid was collected by filtration and washed with 3 L of water, 1 L of acetone, 1 L of tetrahydrofuran, and 1 L of acetone and dried to give 2,9-dimethylpentacene.

Preparation of 2,10-Dimethylpentacene

Preparation of 4,6-Bis(4-methylbenzyl)isophthalic Acid

A mixture of 21.1 grams of 4,6-bis(4-methylbenzoyl)isophthalic acid, 350 mL of acetic acid, and 2.10 grams of 5% palladium on carbon (as a catalyst) was heated to 65° C. for 17 hours in an atmosphere of hydrogen at 270 kPa. The resulting mixture was filtered through Celite™ diatomaceous earth filter agent to remove the catalyst. The filtrate was concentrated in vacuo to give 4,6-bis(4-methylbenzyl)isophthalic acid.

Preparation of 3,9-Dimethylpentacene-5,7(12H,14H)-dione

To 14.1 grams of 4,6-bis(4-methylbenzyl)isophthalic acid was added 75 mL of trifluoroacetic acid followed by 48 grams of trifluoromethanesulfonic acid. After stirring for 3 days at room temperature, the mixture was poured over 200 g of ice, and the resulting solid was collected by filtration. The solid was washed with 400 mL of saturated aqueous sodium bicarbonate solution, followed by 1100 mL of water until the filtrate was neutral to pH paper. The solid was washed with heptane and dried to give 3,9-dimethylpentacene-5,7(12H,14H)-dione.

Preparation of 2,10-Dimethylpentacene

A mixture of 1 gram of 3,9-dimethylpentacene-5,7(12H,14H)-dione and 10 mL of 2-methoxyethyl ether was stirred and flushed with nitrogen for 15 minutes. To this was added 0.948 grams of sodium borohydride and stirring was continued at room temperature overnight. To the mixture was added 6.3 mL of methanol and stirring was continued for 1.5 hours at room temperature. To the mixture was added 15 mL of acetic acid and 10 mL of concentrated hydrochloric acid. The mixture was stirred for one hour at room temperature followed by heating for one hour at 60° C. To the mixture was added 50 mL of water and the solid was isolated by filtration and washed with water. The solid was washed with tetrahydrofuran until a pale filtrate resulted. The resulting solid was washed with heptane and dried under an atmosphere of nitrogen to give 2,10-dimethylpentacene.

Solubility Characteristics of Substituted Pentacenes

The solubility of several alkyl substituted pentacenes in tetrahydrofuran (THF) was compared with that of pentacene. Samples were prepared by adding excess alkyl substituted pentacene compounder pentacene compound to newly opened THF and sonicating for 20–30 seconds to facilitate dissolution. All handling of the solutions and solvent was done in a nitrogen-purged environment. Solutions were transferred to a 1 cm cuvette with a disposable pipette. The cuvette was then placed in a spectrophotometer for 5 minutes for temperature equilibration (25° C.). Absorbance measurements were made using an Hewlett Packard 8453 photodiode array spectrophotometer over a range of wavelengths from 200 to 1100 nm. THF was used as a reference blank. All of the spectrographs were corrected for baseline differences, which possibly resulted from excess compound in suspension. In calculating the concentration and weight % values, the extinction coefficient of pentacene that is, $10^{3.76}$ at 577 nm was used for all substituted pentacenes. The results are shown below in Table 1.

TABLE 1

Solubility of Pentacene and Alkyl Substituted Pentacenes in THF

| Alkyl Substitution | Absorbance at 577 nm | Relative Absorbance | Concentration (M) | Weight % |
|---|---|---|---|---|
| 2,9-dimethyl | 0.021 | 0.142 | $3.59 \times 10^{-6}$ | $1.64 \times 10^{-4}$ |
| 2,10-dimethyl | 0.035 | 0.239 | $6.06 \times 10^{-6}$ | $2.77 \times 10^{-4}$ |
| 2,9-dihexyl | 0.987 | 6.752 | $1.72 \times 10^{-4}$ | $8.62 \times 10^{-3}$ |
| 2,9-dinonyl | 1.398 | 9.562 | $2.43 \times 10^{-4}$ | $1.45 \times 10^{-2}$ |
| 2,9-didodecyl | 0.061 | 0.420 | $1.07 \times 10^{-5}$ | $7.38 \times 10^{-4}$ |
| 2,9-di(3,3,5-trimethylhexyl) | — | — | $3.35 \times 10^{-3}$ | $2.00 \times 10^{-1}$ |
| None (pentacene) | 0.146 | 1.000 | $2.54 \times 10^{-5}$ | $7.95 \times 10^{-4}$ |

The results in Table 1 show that the 2,9-dinonylpentacene, 2,9-dihexylpentacene, and 2,9-di(3,5,5-trimethylhexyl) pentacene were significantly more soluble in THF than pentacene, 2,9-dimethylpentacene, 2,10-dimethylpentacene, or 2,9-didodecylpentacene.

Example 9

Purification of 2,9-Dimethylpentacene 2,9-Dimethylpentacene was purified in a 3-zone furnace (Thermolyne 79500 tube furnace from Barnstead Thermolyne, Dubuque, Iowa) at reduced pressure under a constant flow of nitrogen gas.

Preparation of Organic Thin Film Transistors

Single crystal <100> orientation silicon wafers were obtained from Silicon Valley Microelectronics, Inc., San Jose, Calif. Either a 1500 Å layer of aluminum oxide or a 1000 Å silicon oxide layer was deposited on each wafer front via chemical vapor deposition methods. A 5000 Å layer of aluminum metal was vapor deposited onto the backside of each wafer. These doped wafers capped with aluminum served as gate electrodes, and the aluminum oxide or silicon oxide functioned as the gate dielectric for the organic thin film transistors prepared below.

A silicon oxide coated silicon wafer substrate described above was cleaned using consecutive rinses of acetone, methanol, 2-propanol, and de-ionized water, followed by heating for 3 minutes at 100° C. on a hot plate and a 15-minute exposure in a UV/ozone chamber (home-built, short-wavelength UV). The purified 2,9-dimethylpentacene was deposited by sublimation under vacuum (approximately $10^{-6}$ Torr (or $1.33 \times 10^{-4}$ Pa)) onto the silicon oxide gate dielectric at a rate of 0.5 Å per second to reach a final thickness of 500 Å as measured by a quartz crystal microbalance. Palladium or gold source and drain electrodes were then shadow masked onto the 2,9-dimethylpentacene layer. In the resulting device the gap between the source and drain electrodes served as a channel for the semiconductor and was dimensioned 40 µm in length (L) (distance between source and drain electrodes) by 1000 µm in width (W).

Performance Testing of Organic Thin Film Transistor

Transistor performance of the resulting organic thin film transistors (OTFTs) was tested at room temperature in air using techniques known in the art, for example as described in S. M., Sze, Physics of Semiconductor *Physics Devices*, page 442, John Wiley and Sons, New York (1981), the description of which is incorporated herein by reference. Typically the source-drain current in the transistor's saturation mode was measured and is given by the following equation:

$$I_d \cong (2mW/L)\mu_p C_1 (V_g - V_t)^2$$

where $I_d$=drain current,
m is a parameter dependent on doping concentrations, and is 1 here,
W=channel width,
L=channel length,
$\mu_p$=mobility (cm$^2$/Vs),
$C_1$=specific gate capacitance (for 1000 angstrom SiO$_2$, $C_1$=0.000345 pF/$\mu$m$^2$),
$V_g$=gate-source bias voltage, and
$V_t$=threshold voltage.
A Semiconductor Parameter Analyzer (model 4145A from Hewlett Packard, San Jose, Calif.) was used to obtain the results set forth below.

Example 12

Example 9 was repeated except that 2,9-dihexylpentacene was used instead of 2,9-dimethylpentacene. The results appear below in Table 2.

Comparative Example C1

Example 9 was repeated except that pentacene was used instead of 2,9-dimethylpentacene. The results appear below in Table 2.

Comparative Example C2

Comparative Example 1 was repeated except that the purified pentacene was deposited on an aluminum oxide gate dielectric instead of the silicon oxide dielectric. The results appear below in Table 2.

TABLE 2

Performance of OTFTs

| Ex. No. | Semiconductor | Gate Dielectric | Charge-Carrier Mobility (cm$^2$/Vs) | Threshold Voltage (V) | Sub-Threshold Slope (V/decade) | On/Off Ratio |
|---|---|---|---|---|---|---|
| 7 | 2,9-Dimethyl pentacene | SiO$_2$ | 0.344 | −11.51 | 3.318 | 1.93E+05 |
| 8 | 2,9-Dimethyl pentacene | Al$_2$O$_3$ | 0.680 | +0.01 | 2.241 | 3.53E+04 |
| 10 | 2,9-Dihexyl pentacene | SiO$_2$ | 0.251 | +1.28 | 4.652 | 3.15E+03 |
| C1 | Pentacene | SiO$_2$ | 0.297 | −8.46 | 4.12 | 1.66E+05 |
| C2 | Pentacene | Al$_2$O$_3$ | 0.972 | −6.71 | 1.72 | 1.88E+07 |

The square root of the drain current ($I_d$) was plotted as a function of gate-source bias ($V_g$), from +10V to −40V for a constant source-drain bias ($V_d$) of −40V, and the saturation field effect mobility, $\mu_p$, was calculated from the straight line portion of the curve using the specific capacitance of the gate dielectric, the channel width, and the channel length. The x-axis extrapolation of this straight-line fit was taken as the threshold voltage ($V_t$). In addition, plotting $I_d$ as a function of $V_g$ yielded a curve where a straight line fit was drawn along a portion of the curve containing $V_t$. The inverse of the slope of this line was the sub-threshold slope (S). The on-off ratio was taken as the difference between the minimum and maximum values of the $I_d$-$V_g$ curve.

Multiple 2,9-dimethylpentacene OTFTs were prepared, and a representative sample of OTFTs was tested for each deposition run. The averaged results appear below in Table 2.

Example 10

Example 9 was repeated except that the purified 2,9-dimethylpentacene was deposited onto an aluminum oxide gate dielectric instead of the silicon oxide gate dielectric. The results appear below in Table 2.

Example 11

OTFTs were made as in Example 9 except that 2,10-dimethylpentacene was used instead of 2,9-dimethylpentacene.

The results in Table 2 show that 2,9-dimethylpentacene and 2,9-dihexylpentacene semiconductor layers exhibited high mobility values that are unexpectedly comparable to those of pentacene.

Example 13

This example shows the surprising solvent resistance of the 2,9-dimethylpentacene semiconductor layer in an organic thin film transistor. OTFTs with 2,9-dimethylpentacene semiconductor layers were prepared and tested for mobility as in Examples 9 and 10. Several small drops of 2-propanol were placed in the active area (on the semiconductor layer in the channel between the source and drain pads) of each OTFT. After allowing the solvent to evaporate, each OTFT was observed for physical changes and again tested for mobility. The resulting 2,9-dimethylpentacene layers on both silicon oxide and aluminum oxide appeared unchanged. The mobility of 2,9-dimethylpentacene on aluminum oxide was unchanged, while that on silicon oxide was decreased by a factor of about two

Comparative Example C3

OTFTs with pentacene semiconductor layers were prepared and tested for charge-carrier mobility as in Comparative Examples C1 and C2. Several small drops of 2-propanol were placed in the active area (on the semiconductor layer in the channel between the source and drain pads) of each OTFT. After the solvent was allowed to evaporate, each OTFT was observed for physical changes and again tested for mobility. The resulting pentacene layers on both silicon oxide and aluminum oxide had numerous cracks, and the source and drain electrodes on the pentacene had popped off. These OTFT devices were not functional.

The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A substituted pentacene compound comprising at least one substituent selected from the group consisting of alkyl groups, alkoxy groups, thioalkoxy groups, halogen substituents, and combinations thereof; said substituent(s) each being bonded to at least one carbon atom of pentacene selected from the number 1, 2, 3, 4, 8, 9, 10, and 11 carbon atoms, and being the only substituent(s); with the proviso that when said compound has only two said substituents, both of which are methyl or alkoxy, and one said substituent is bonded to said number 2 carbon atom, the other said substituent, if methyl, is bonded to said number 1, 3, 4, 8, or 11 carbon atom and, if alkoxy, is bonded to said number 1, 3, 4, 8, 9, or 11 carbon atom; and with the further proviso that when said compound has only four said substituents, all of which are alkoxy, said substituents are bonded to said numbers 2, 3, 9, and 10 carbon atoms.

2. The compound of claim 1 wherein said compound has only two said substituents.

3. The compound of claim 2 wherein said substituents are bonded to different terminal rings of pentacene.

4. The compound of claim 3 wherein said substituents are bonded to the numbers 2 and 9 carbon atoms or the numbers 2 and 10 carbon atoms.

5. The compound of claim 4 wherein said substituents are bonded to the numbers 2 and 9 carbon atoms.

6. The compound of claim 1 wherein each said substituent is independently selected from the group consisting of alkyl groups, alkoxy groups, and combinations thereof.

7. The compound of claim 1 wherein each said substituent is an alkyl group.

8. The compound of claim 1, wherein said compound is represented by the following general formula:

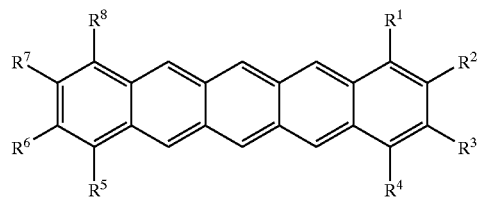

wherein each R group is independently selected from the group consisting of alkyl groups, alkoxy groups, thioalkoxy groups, halogen atoms, hydrogen atoms, and combinations thereof.

9. The compound of claim 8 wherein each said R group is independently selected from the group consisting of alkyl groups, alkoxy groups, hydrogen atoms, and combinations thereof.

10. The compound of claim 9 wherein each said R group is independently selected from the group consisting of alkyl groups and hydrogen atoms.

11. The compound of claim 10 wherein each said R group is independently selected from the group consisting of methyl, n-hexyl, n-nonyl, n-dodecyl, sec-butyl, 3,5,5-trimethylhexyl, 2-ethylhexyl, and hydrogen.

12. The compound of claim 8 wherein said $R^2$ and said $R^6$ are independently selected from the group consisting of alkyl groups, alkoxy groups, thioalkoxy groups, halogen atoms, and combinations thereof; and said $R^1$, $R^3$, $R^4$, $R^5$, $R^7$, and $R^8$ are hydrogen atoms.

13. The compound of claim 8 wherein said $R^2$ and said $R^7$ are independently selected from the group consisting of alkyl groups, alkoxy groups, thioalkoxy groups, halogen atoms, and combinations thereof; and said $R^1$, $R^3$, $R^4$, $R^5$, $R^6$, and $R^8$ are hydrogen atoms.

14. The compound of claim 12 wherein said $R^2$ and said $R^6$ are independently selected from the group consisting of alkyl groups, alkoxy groups, and combinations thereof.

15. The compound of claim 13 wherein said $R^2$ and said $R^7$ are independently selected from the group consisting of alkyl groups, alkoxy groups, and combinations thereof.

16. The compound of claim 14 wherein said $R^2$ and said $R^6$ are independently alkyl.

17. The compound of claim 15 wherein said $R^2$ and said $R^7$ are independently alkyl.

18. 1,4,8,11-Tetramethylpentacene; 2,9-dihexylpentacene; 2,10-dihexylpentacene; 2,9-dinonylpentacene; 2,10-dinonylpentacene; 2,9-didodecylpentacene; 2,10didodecylpentacene; 2,9-di-sec-butylpentacene; 2,10-di-sec-butylpentacene; 2,9-di-3,5,5-trimethylhexylbenzene; 2,10-di-3,5,5-trimethylhexylpentacene; 2,9-di-2-ethylhexylpentacene; and 2,10-di-2-ethylhexylpentacene.

19. A semiconductor device comprising at least one compound of claim 1.

20. A semiconductor device comprising at least one compound of claim 8.

21. A semiconductor device comprising at least one compound of claim 12.

22. A semiconductor device comprising at least one compound of claim 13.

23. A semiconductor device comprising at least one compound selected from the group consisting of the compounds of claim 17, 2,9-dimethylpentacene, 2,10-dimethylpentacene, 2,10-dialkoxypentacenes, and 1,4,8,11-tetraalkoxypentacenes.

24. An article comprising the device of claim 19, claim 20, claim 21, claim 22, or claim 23.

* * * * *

UNITED STATES PATENT AND TRADEMARK OFFICE
CERTIFICATE OF CORRECTION

PATENT NO.      : 6,864,396 B2
DATED           : March 8, 2005
INVENTOR(S)     : Smith, Terrance P.

It is certified that error appears in the above-identified patent and that said Letters Patent is hereby corrected as shown below:

Column 11,
Lines 40 and 63, delete "AlCl3" and insert -- $AlCl_3$ --.

Column 14,
Lines 20-30, (Reaction Scheme C), delete

"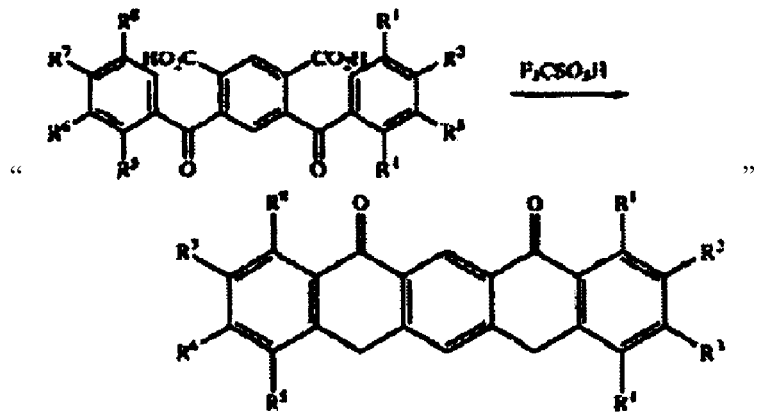"

and insert

-- 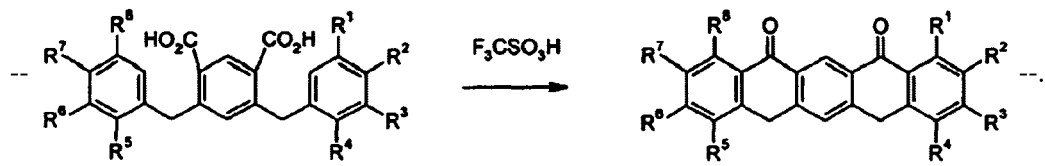 --.

Column 30,
Line 59 after "two" insert -- . --.

UNITED STATES PATENT AND TRADEMARK OFFICE
CERTIFICATE OF CORRECTION

PATENT NO. : 6,864,396 B2
DATED : March 8, 2005
INVENTOR(S) : Smith, Terrance P.

It is certified that error appears in the above-identified patent and that said Letters Patent is hereby corrected as shown below:

Column 32,
Line 39, delete "2,10" and insert -- 2,10- --.
Line 41, delete "trimethylhexylbenzene" and insert -- trimethylhexylpentacene --.

Signed and Sealed this

Twentieth Day of December, 2005

JON W. DUDAS
*Director of the United States Patent and Trademark Office*